(12) United States Patent
Ji et al.

(10) Patent No.: US 11,949,072 B2
(45) Date of Patent: Apr. 2, 2024

(54) SILICON-BASED ENERGY STORAGE DEVICES WITH ELECTROLYTE CONTAINING CYANATE BASED COMPOUNDS

(71) Applicant: Enevate Corporation, Irvine, CA (US)

(72) Inventors: Liwen Ji, San Diego, CA (US); Benjamin Yong Park, Mission Viejo, CA (US); Younes Ansari, Irvine, CA (US); Hong Zhao, Aliso Viejo, CA (US)

(73) Assignee: Enevate Corporation, Irvine, CA (US)

( * ) Notice: Subject to any disclaimer, the term of this patent is extended or adjusted under 35 U.S.C. 154(b) by 439 days.

(21) Appl. No.: 16/780,120

(22) Filed: Feb. 3, 2020

(65) Prior Publication Data
US 2021/0249689 A1    Aug. 12, 2021

(51) Int. Cl.
*H01M 10/0569* (2010.01)
*C07C 261/02* (2006.01)
*H01M 4/02* (2006.01)
*H01M 4/38* (2006.01)
*H01M 10/0567* (2010.01)
*H01M 10/0568* (2010.01)

(52) U.S. Cl.
CPC ....... *H01M 10/0569* (2013.01); *C07C 261/02* (2013.01); *H01M 4/386* (2013.01); *H01M 10/0567* (2013.01); *H01M 10/0568* (2013.01); *H01M 2004/027* (2013.01); *H01M 2300/0037* (2013.01)

(58) Field of Classification Search
CPC ......... H01M 10/0569; H01M 10/0567; H01M 10/0568; H01M 2004/027; H01M 4/386; H01M 2300/0037
See application file for complete search history.

(56) References Cited

U.S. PATENT DOCUMENTS

| | | | |
|---|---|---|---|
| 11,296,357 B2 * | 4/2022 | Nakazawa | ........ H01M 10/0569 |
| 2015/0125761 A1 | 5/2015 | Shimamoto et al. | |
| 2016/0164143 A1 | 6/2016 | Sawa et al. | |
| 2017/0187071 A1 | 6/2017 | Wang et al. | |

(Continued)

FOREIGN PATENT DOCUMENTS

| | | | | |
|---|---|---|---|---|
| CN | 108676138 | * | 10/2018 | ........... C08G 18/307 |
| JP | 2002008667 | * | 1/2002 | .............. H01M 4/86 |
| JP | 2013033663 | * | 2/2013 | .......... H01M 10/052 |

OTHER PUBLICATIONS

Machine Translation of Kanako (Year: 2013).*

(Continued)

*Primary Examiner* — Matthew T Martin
*Assistant Examiner* — Ankith R Sripathi
(74) *Attorney, Agent, or Firm* — McAndrews, Held & Malloy, Ltd.

(57) ABSTRACT

Electrolytes and electrolyte additives for energy storage devices comprising cyanate based compounds are disclosed. The energy storage device comprises a first electrode and a second electrode, wherein at least one of the first electrode and the second electrode is a Si-based electrode, a separator between the first electrode and the second electrode, an electrolyte comprising at least two electrolyte co-solvents, wherein at least one electrolyte co-solvent comprises a cyanate based compound.

14 Claims, 7 Drawing Sheets

(56) References Cited

U.S. PATENT DOCUMENTS

2018/0375094 A1    12/2018    He et al.

OTHER PUBLICATIONS

Machine Translation of Fanhou (Year: 2018).*
Machine Translation of Endo (Year: 2002).*
International Preliminary Report on Patentability, PCT/US2021/014166, dated Aug. 18, 2022, 9 pages.
International Search Report, PCT/US2021/014166 dated Jul. 9, 2021, 12 pages.

* cited by examiner

SILICON-BASED ENERGY STORAGE DEVICES WITH ELECTROLYTE CONTAINING CYANATE BASED COMPOUNDS

BACKGROUND

Field

The present application relates generally to electrolytes for energy storage devices. In particular, the present application relates to electrolytes and additives for use in lithium-ion energy storage devices with silicon-based anode materials.

Description of the Related Art

As the demands for both zero-emission electric vehicles and grid-based energy storage systems increase, lower costs, high energy density, high power density, and safety of energy storage devices, such as lithium (Li)-ion batteries, are highly desirable. Improving the energy and power density and the safety of Li-ion batteries requires the development of high-capacity high-voltage cathodes, high-capacity anodes, and accordingly, functional electrolytes with high voltage stability and interfacial compatibility with electrodes.

A Li-ion battery typically includes a separator and/or electrolyte between an anode and a cathode. In one class of the battery, the separator, cathode and anode materials are individually formed into sheets or films. Sheets of the cathode, separator and anode are subsequently stacked or rolled with the separator separating the cathode and the anode (collectively, electrodes) to form a battery. A typical electrode includes electro-chemically active material layer on an electrically conductive metal (e.g., aluminum or copper). Films can be rolled, or cut into pieces which are then layered into stacks. The stack includes alternating electro-chemically active materials with the separator between them.

Silicon (Si) is one of the most promising anode materials for Li-ion batteries due to its high specific gravimetric and volumetric capacity (3579 mAh/g and 2194 mAh/cm$^3$ vs. 372 mAh/g and 719 mAh/cm$^3$ for graphite), and low lithiation potential (<0.4 V vs. Li/Li$^+$). Among the various cathodes presently available, layered lithium transition-metal oxides such as Ni-rich Li[Ni$_x$Co$_y$Mn(Al)$_{1-x-y}$]O$_2$ (NCM or NCA) are the most promising cathodes due to their high theoretical capacity (~280 mAh/g) and relatively high average operating potential (3.6 V vs Li/Li$^+$). In addition to Ni-rich NCM or NCA cathode, LiCoO$_2$ (LCO) is also a very attractive cathode material because of its relatively high theoretical specific capacity of 274 mAh g$^{-1}$, high theoretical volumetric capacity of 1363 mAh cm$^{-3}$, low self-discharge, high discharge voltage, and good cycling performance. Coupling Si-based anodes with high-voltage Ni-rich NCM (or NCA) or LCO cathodes can deliver more energy than conventional Li-ion batteries with graphite-based anodes, due to the high capacity of these new electrodes. However, both Si-based anodes and high-voltage Ni-rich NCM (or NCA) or LCO cathodes face formidable technological challenges, and long-term cycling stability with high-Si anodes paired with NCM or NCA cathodes has yet to be achieved.

For anodes, Si-based materials can provide significant improvement in energy density. However, the large volumetric expansion (>300%) during the Li alloying/de-alloying processes can lead to disintegration of the active material and the loss of electrical conduction paths, thereby reducing the cycling life of the battery. In addition, an unstable solid electrolyte interphase (SEI) layer can develop on the surface of the cycled anodes. As the active material expands and contracts during each charge-discharge cycle, unreacted Si surfaces in the active material can subsequently be exposed to the liquid electrolyte and form thicker SEI layers. This results in an irreversible capacity loss at each cycle due to the reduction at the low potential where the liquid electrolyte reacts with the exposed unreacted surface of the Si in the anode. In addition, oxidative instability of the conventional non-aqueous electrolyte takes place at voltages beyond 4.5 V, which can lead to accelerated decay of cycling performance. Because of the generally inferior cycle life of Si compared to graphite, only a small amount of Si or Si alloy is used in conventional anode materials.

The NCM (or NCA) or LCO cathode usually suffers from an inferior stability and a low capacity retention at a high cut-off potential. The reasons can be ascribed to the unstable surface layer's gradual exfoliation, the continuous electrolyte decomposition, and the transition metal ion dissolution into electrolyte solution. The major limitations for LCO cathode are high cost, low thermal stability, and fast capacity fade at high current rates or during deep cycling. LCO cathodes are expensive because of the high cost of Co. Low thermal stability refers to exothermic release of oxygen when a lithium metal oxide cathode is heated. In order to make good use of Si-based anode//NCM or NCA cathode and Si-based anode//LCO cathode Li-ion battery systems, the aforementioned barriers need to be overcome.

The majority of electrolytes for Si anode-based Li-ion batteries literatures are carbonate-based solutions with LiPF$_6$ salt dissolved in the mixture of cyclic alkyl carbonate (such as ethylene carbonate (EC), vinylene carbonate (VC), propylene carbonate (PC), etc.) and one or more linear carbonates (such as ethylene methyl carbonate (EMC), dimethyl carbonate (DMC), diethyl carbonate (DEC), etc.) with/without small amounts of additives. In recent years, fluoroethylene carbonate (FEC) has been frequently used as an additive, co-solvent, or even main solvent in the Si anode-based Li-ion batteries. However, high FEC-containing electrolyte formulation-based cells suffer from gas generation and volume swelling due to the decomposition of FEC phase upon prolonged cycling. High FEC-containing electrolyte formulations also have a high viscosity which can reduce cell rate performance and the performance at extreme conditions. In addition, FEC is relatively expensive. Thus, different additives and/or co-solvents for Si anode-based.

SUMMARY

In one aspect, an energy storage device is described. The energy storage device includes a first electrode, a second electrode, a separator between the first electrode and the second electrode, and an electrolyte system. The electrolyte system includes a cyanate based compound, a linear carbonate, a cyclic carbonate, and a Li-containing salt.

In some embodiments, the cyanate based compound is any one of formulae (I), (II), (III), (IV), (V), (VI), (VII) and (VIII):

-continued

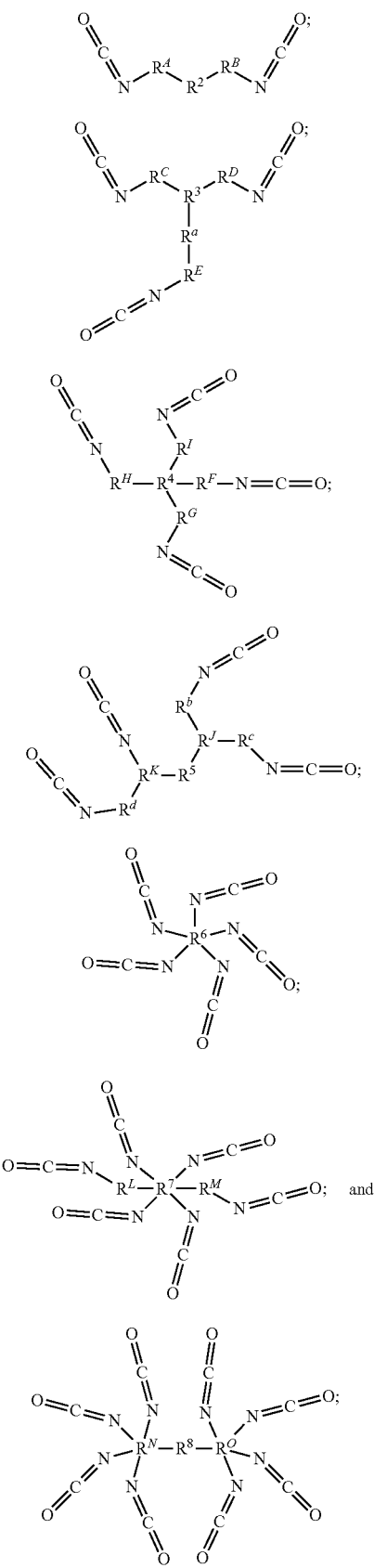

wherein R¹ is selected from the group consisting of a $C_1$-$C_8$ alkyl, a $C_2$-$C_8$ alkenyl, a $C_2$-$C_8$ alkynyl, a cycloalkyl, an aryl, a heteroalkenyl,

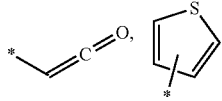

and

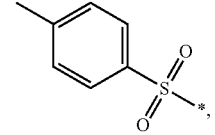

wherein R¹ may be optionally substituted by —F, alkyl, alkenyl, cycloalkyl, aryl, —CN, —N⁺C—, fluoro-alkyl, fluoro-ether, —N(CH₃)₂,

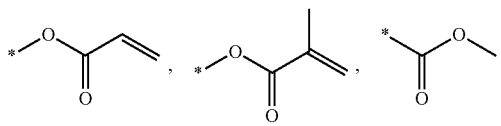

and

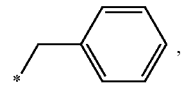

wherein $R^2$, $R^3$, $R^4$, $R^5$, $R^6$, $R^7$ and $R^8$ are each independently selected from the group consisting of a $C_1$-$C_8$ alkylene, a $C_2$-$C_8$ alkenylene, a $C_2$-$C_8$ alkynylene, a cycloalkylene, an arylene, —O—,

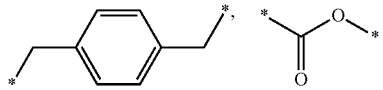

and

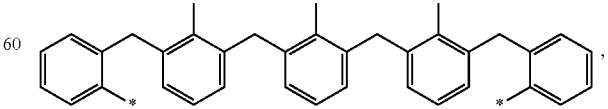

wherein $R^2$, $R^3$, $R^4$, $R^5$, $R^6$, $R^7$ and $R^8$ may be optionally substituted by —F, alkyl, alkenyl, cycloalkyl, aryl, —CN, —N⁺C⁻, fluoro-alkyl, fluoro-ether, —N(CH₃)₂,

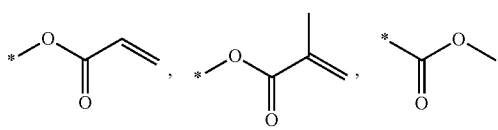

and

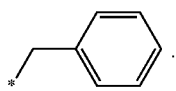

wherein $R^A$, $R^B$, $R^C$, $R^D$, $R^E$, $R^F$, $R^G$, $R^H$, $R^I$, $R^J$, $R^K$, $R^L$, $R^M$, $R^N$ and $R^O$ are each independently selected from the group consisting of a bond, a $C_1$-$C_8$ alkylene, a cycloalkylene, an arylene and —Si—, wherein $R^A$, $R^B$, $R^C$, $R^D$, $R^E$, $R^F$, $R^G$, $R^H$, $R^I$, $R^J$, $R^K$, $R^L$, $R^M$, $R^N$ and $R^O$ may be optionally substituted by —F, alkyl, alkenyl, alkynyl and aryl, and wherein $R^a$, $R^b$, $R^c$ and $R^d$ are each independently selected from the group consisting of a bond, a $C_1$-$C_8$ alkylene, a $C_2$-$C_8$ alkenylene, a $C_2$-$C_8$ alkynylene, and

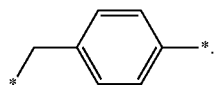

In some embodiments, the cyanate based compound is selected from the group consisting of allyl isocyanate; vinyl isocyanate; 1-isocyanatoprop-1-ene; (E)-1-isocyanatoprop-1-ene; 4-isocyanatobut-1-ene; 1-isocyanato-2-methylprop-1-ene; 1-isocyanato-3-methylbut-2-ene; 3-isocyanatobut-1-ene; 3-isocyanato-3-methylbut-1-ene; Isocyanatosulfanylethene; 3-isocyanatosulfanylprop-1-ene; Isocyanatooxyethene; 3-isocyanatoprop-1-yne; 3-isocyanato-3-methylbut-1-yne; 4-isocyanatobut-1-yne; 1-fluoro-2-isocyanatocyclopropane; Isocyanatomethylcyclopropane; (1S, 2R)-1-fluoro-2-isocyanatocyclopropane; 1-fluoro-2-isocyanatoethane; 1-isocyanatopropa-1,2-diene; (1Z)-1-isocyanatobuta-1,3-diene; 2-isocyanatoethenone; 6-isocyanatohexanenitrile; 6-isocyanatohexyl cyanate; 2,4-difluoro-1,6-diisocyanatohexane; 3,3,4,4-tetrafluoro-1,6-diisocyanatohexane; Thien-2-yl isocyanate; Thien-3-yl isocyanate; 2-Methacryloyloxyethyl isocyanate (CAS: 30674-80-7); 1-Isocyanatoethyl methacrylate; 2-Isocyanatoethyl Acrylate (CAS: 13641-96-8); Phenyl isocyanate; 4-(Trifluoromethoxy)phenyl isocyanate; 4-(Trifluoromethyl)phenyl isocyanate; 3,5-Bis(trifluoromethyl)phenyl isocyanate; 2-Fluoro-1-isocyanato-3-(trifluoromethyl)benzene; 1-(Difluoromethoxy)-4-isocyanatobenzene; 4-isocyanato-N,N-dimethylaniline; 4-methylbenzene-1-sulfonyl isocyanate; 1-isocyanato-2-phenylbenzene; 1-isocyanato-4-phenylbenzene; 1-ethenyl-4-isocyanatobenzene; 1-isocyanato-4-prop-2-enylbenzene; 1-isocyanato-4-prop-1-en-2-ylbenzene; 1-cyclopentyl-4-isocyanatobenzene; 1-cyclopropyl-4-isocyanatobenzene; 1-isocyanato-4-[(4-isocyanophenyl)methyl]benzene; Diisocyanatomethane; 1,2-diisocyanatoethane; 1,3-diisocyanatopropane; 2-fluoro-1,3-diisocyanatopropane; 1,4-diisocyanatobutane; 1,5-pentane diisocyanate; 1,6-diisocyanatohexane; 1,6-Diisocyanato-2-methylhexane; methyl 2,6-diisocyanatohexanoate; Isophorone diisocyanate; 2,3-diisocyanato-7-methylbicyclo[2.2.1]heptane; 4,4'-diisocyanatodicyclohexylmethane; TCD-diisocyanate (28807-72-9); 1,2-Diisocyanatobenzene; 1,3-Phenylene diisocyanate; 1,4-Diisocyanatobenzene; Toluene diisocyanate; Tetramethylxylene diisocyanate; 1-isocyanato-4-(2-isocyanatopropan-2-yl)benzene; 1-isocyanato-4-(4-isocyanatophenyl)benzene; 1-isocyanato-3-(4-isocyanatophenyl)benzene; 1-isocyanato-4-(4-isocyanato-3-methylphenyl)-2-methylbenzene; 1-isocyanato-4-(4-isocyanatocyclohexyl)benzene; 1-isocyanato-4-[(4-isocyanatophenyl)methyl]benzene; 1-isocyanato-2-[(4-isocyanatophenyl)methyl]benzene; 1-isocyanato-3-[(3-isocyanatophenyl)methyl]benzene; 1-isocyanato-4-[(4-isocyanatocyclohexyl)methyl]benzene; 1-isocyanato-4-[(4-isocyanatophenyl)methyl]-2-methylbenzene; 1-isocyanato-4-[(4-isocyanato-3-methylphenyl)methyl]-2-methylbenzene; 4-isocyanato-2-[(4-isocyanatophenyl)methyl]-1-methylbenzene; 1-isocyanato-2-[(2-isocyanatophenyl)methyl]benzene; 4-isocyanato-1-(4-isocyanato-2-methylphenyl)-2-methylbenzene; 1-isocyanato-4-[1-(4-isocyanatophenyl)ethyl]benzene; 1-isocyanato-4-[2-(4-isocyanatophenyl)propan-2-yl]benzene; 1,4-bis(4-isocyanatophenyl)benzene; 1,4-bis[(4-isocyanatophenyl)methyl]benzene; 1-isocyanato-4-[1-(4-isocyanatophenyl)ethenyl]benzene; 1-isocyanato-2-[(E)-2-(4-isocyanatophenyl)ethenyl]benzene; 1-isocyanato-4-[(E)-2-(4-isocyanatophenyl)ethenyl]benzene; 1-isocyanato-4-[(E)-1-(4-isocyanatophenyl)prop-1-en-2-yl]benzene; (Z)-2,3-bis(4-isocyanatophenyl)prop-2-enenitrile; 1-isocyanato-4-[2-(4-isocyanatophenyl)ethynyl]benzene; 1-isocyanato-4-[1,1,2,2-tetrafluoro-2-(4-isocyanatophenyl)ethyl]benzene; 1-isocyanato-4-[1-(4-isocyanatophenyl)cyclopropyl]benzene; 1-[cyclohexyl-(4-isocyanatophenyl)methyl]-4-isocyanatobenzene; 2-isocyanato-5-[(4-isocyanatophenyl)methyl]-1,3-bis(prop-2-enyl)benzene; 1-isocyanato-2-(2-isocyanato-5-prop-2-enylphenyl)-4-prop-2-enylbenzene; 1,1,2-triisocyanatoethane; 1,1,3-triisocyanatopropane; 1,1,5-triisocyanatopentane; 1,2,6-triisocyanatohexane; 1,3,6-triisocyanatohexane; 1,4,7-triisocyanatoheptane; 1,1,6-triisocyanatohexane; 2-isocyanatoethyl (2S)-2,6-diisocyanatohexanoate; 2-isocyanatoethyl 2,6-diisocyanatohexanoate; 4-isocyanatobutyl 2,6-diisocyanatohexanoate; 1-[diisocyanato(phenyl)methyl]-2-isocyanatobenzene; 2,4-diisocyanato-1-[(4-isocyanatophenyl)methyl]benzene; 1,4-diisocyanato-2-[(4-isocyanatophenyl)methyl]benzene; 1-isocyanato-4-[isocyanato-(4-isocyanatophenyl)methyl]benzene; 1-[bis(4-isocyanatophenyl)methyl]-4-isocyanatobenzene; 1-[1,3-bis(4-isocyanatophenyl)propan-2-yl]-4-isocyanatobenzene; 2-benzyl-1,3,5-triisocyanatobenzene; 2,4-diisocyanato-1-[(4-isocyanatophenyl)-phenylmethyl]benzene; 1,1,1,5-tetraisocyanatohexane; 1,1,1,6-tetraisocyanatohexane; 1,1,6,6-tetraisocyanatohexane; 1-[diisocyanato-(4-isocyanatophenyl)methyl]-4-isocyanatobenzene; 4,4'-Benzylidenebis(6-methyl-m-phenylene) tetraisocyanate; 1,5-diisocyanato-2-[[4-isocyanato-3-[(4-isocyanatophenyl)methyl]phenyl]methyl]-4-methylbenzene; 1-(1,3-diisocyanato-3,3-diphenylpropyl)-2,4-diisocyanato-5-propan-2-ylbenzene; 1-[(3,5-diisocyanato-2-methylphenyl)-phenylmethyl]-3,5-diisocyanato-2-methylbenzene; 5-[bis(4-isocyanatophenyl)methyl]-1,3-diisocyanato-2-methylbenzene; 2,6-Bis(2-isocyanato-3-((2-isocyanatophenyl)methyl)benzyl)phenyl isocyanate; [diisocyanato(phenyl)silyl]oxy-diisocyanato-phenylsilane; 2-[diisocyanato(phenyl)silyl]ethyl-diisocyanato-phenylsilane; 1-isocyanato-4-[1,1,3,3-tetraisocyanato-3-(4-isocyanatophenyl)propyl]benzene; and 4,4'-benzylidenebis(6-methyl-m-phenylene) tetraisocyanate, or combinations thereof. In some embodiments, the cyanate based compound comprises allyl isocyanate.

In some embodiments, the linear carbonate is selected from the group consisting of ethyl methyl carbonate (EMC), dimethyl carbonate (DMC), and diethyl carbonate (DEC). In some embodiments, the electrolyte system further comprises a co-solvent selected from the group consisting of methyl acetate (MA), ethyl acetate (EA), methyl propanoate, and gamma butyrolactone (GBL). In some embodiments, the cyclic carbonate is selected from the group consisting of fluoroethylene carbonate (FEC), di-fluoroethylene carbonate (DiFEC), Trifluoropropylene carbonate (TFPC), ethylene carbonate (EC), vinyl carbonate (VC), propylene carbonate (PC), -fluoromethyl-5-methyl-1,3-dioxolan-2-one (F-t-BC), 3,3-difluoropropylene carbonate (DFPC), and 3,3,4,4,5,5,6,6,6-Nonafluorohexyl-1-ene carbonate. In some embodiments, the cyclic carbonate is a fluorine containing cyclic carbonate. In some embodiments, the fluorine containing cyclic carbonate is FEC at a concentration of about 5% or more. In some embodiments, the electrolyte is substantially free of non-fluorine containing cyclic carbonate. In some embodiments, the Li-containing salt is a fluorinated Li salt. In some embodiments, the Li-containing salt has a concentration of about 1 M or more.

In some embodiments, at least one of the first electrode and the second electrode is a Si-base electrode. In some embodiments, the Si-based electrode is an anode. In some embodiments, the anode is a Si-dominant anode. In some embodiments, the anode includes greater than 0% and less than about 99% by weight of Si particles, and greater than 0% and less than about 90% by weight of one or more types of carbon phases, wherein at least one of the one or more types of carbon phases is a substantially continuous phase that holds the composite material film together such that the silicon particles are distributed throughout the composite material film. In some embodiments, the anode comprises greater than 50% and less than about 97% by weight of Si particles.

BRIEF DESCRIPTION OF THE DRAWINGS

FIG. 2A depicts an Oxidation sweep, and FIG. 2B depicts a reduction sweep.

DETAILED DESCRIPTION

Definitions

Figure 1:
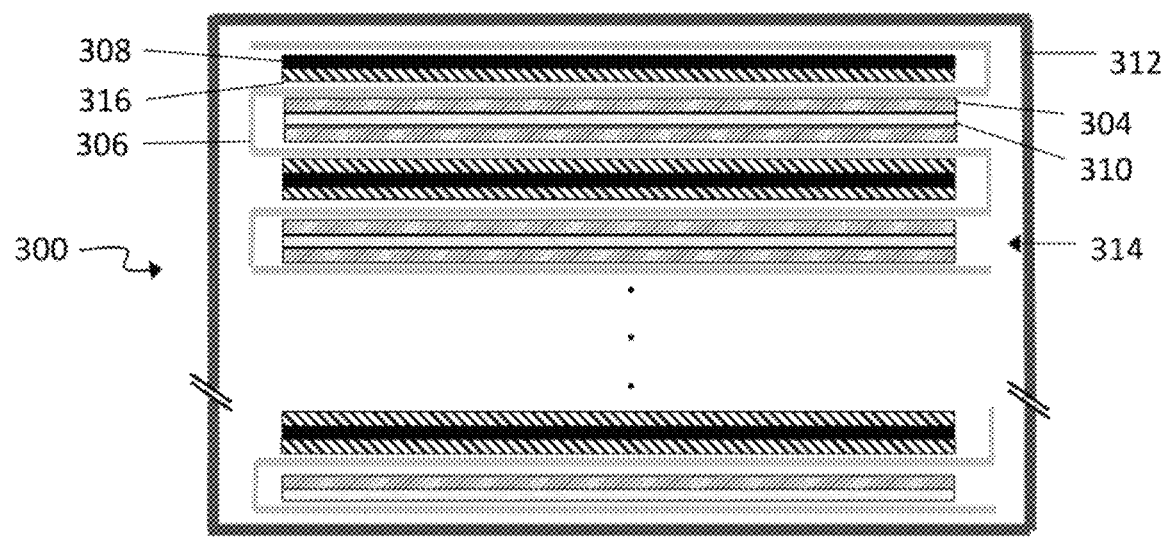
FIG. 1 depicts a cross-sectional schematic diagram of an example of a lithium-ion battery 300 implemented as a pouch cell.

The term "alkyl" refers to a straight or branched, saturated, aliphatic radical having the number of carbon atoms indicated. The alkyl moiety may be branched or straight chain. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 1-11, 1-12 2-3, 2-4, 2-5, 2-6, 3-4, 3-5, 3-6, 4-5, 4-6 and 5-6. The alkyl group is typically monovalent, but can be divalent, such as when the alkyl group links two moieties together.

The term "fluoro-alkyl" refers to an alkyl group where one, some, or all hydrogen atoms have been replaced by fluorine.

The term "alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —$(CH_2)_n$—, where n is 1, 2, 3, 4, 5, 6, 7, 8, 9, or 10. Alkylene groups include, but are not limited to, methylene, ethylene, propylene, isopropylene, butylene, isobutylene, sec-butylene, pentylene and hexylene.

The term "alkoxy" refers to alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "halo-alkoxy" group, or substituted with fluorine to form a "fluoro-alkoxy" group.

The term "alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can also have from 2 to 3, 2 to 4, 2 to 5, 3 to 4, 3 to 5, 3 to 6, 4 to 5, 4 to 6 and 5 to 6 carbons. The alkenyl group is typically monovalent, but can be divalent, such as when the alkenyl group links two moieties together.

The term "alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

The term "alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can also have from 2 to 3, 2 to 4, 2 to 5, 3 to 4, 3 to 5, 3 to 6, 4 to 5, 4 to 6 and 5 to 6 carbons. The alkynyl group is typically monovalent, but can be divalent, such as when the alkynyl group links two moieties together.

The term "alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, butynylene, sec-butynylene, pentynylene and hexynylene.

The term "cycloalkyl" refers to a saturated or partially unsaturated, monocyclic, fused bicyclic, bridged polycyclic, or spiro ring assembly containing from 3 to 12, from 3 to 10, or from 3 to 7 ring atoms, or the number of atoms indicated. Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, $C_3$-$C_8$ cycloalkyl includes cyclopropyl, cyclobutyl, cyclopentyl, cyclohexyl, cyclooctyl, and norbornane. As used herein, the term "fused" refers to two rings which have two atoms and one bond in common. For example, in the following structure, rings A and B are fused

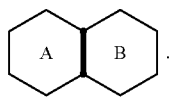

As used herein, the term "bridged polycyclic" refers to compounds wherein the cycloalkyl contains a linkage of one or more atoms connecting non-adjacent atoms. The following structures

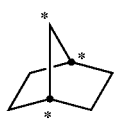

and

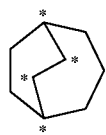

are examples of "bridged" rings. As used herein, the term "spiro" refers to two rings which have one atom in common and the two rings are not linked by a bridge. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, adamantanyl, and norbornanyl; and examples of spiro cycloalkyl groups include spiro[3.3]heptane and spiro[4.5]decane.

The term "cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

The term "aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. Aryl groups may include fused multicyclic ring assemblies wherein only one ring in the multicyclic ring assembly is aromatic. Aryl groups can be mono-, di- or tri-substituted by one, two or three radicals. Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

The term "arylene" refers to an aryl group, as defined above, linking at least two other groups. The two moieties linked to the arylene are linked to different atoms of the arylene. Arylene groups include, but are not limited to, phenylene.

The term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

The term "heteroalkyl" refers to an alkyl group having from 1 to 3 heteroatoms such as N, O and S. The heteroatoms can also be oxidized, such as, but not limited to, —S(O)— and —S(O)$_2$—. For example, heteroalkyl can include ethers, thioethers, alkyl-amines and alkyl-thiols.

The term "heteroalkylene" refers to a heteroalkyl group, as defined above, linking at least two other groups. The two moieties linked to the heteroalkylene can be linked to the same atom or different atoms of the heteroalkylene.

The term "heteroalkenyl" refers to an alkenyl group having from 1 to 3 heteroatoms such as N, O and S. The heteroatoms can also be oxidized, such as, but not limited to, —S(O)— and —S(O)$_2$—.

The term "heterocycloalkyl" refers to a ring system having from 3 ring members to about 20 ring members and from 1 to about 5 heteroatoms such as N, O and S. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

The term "heterocycloalkylene" refers to a heterocyclalkyl group, as defined above, linking at least two other groups. The two moieties linked to the heterocycloalkylene can be linked to the same atom or different atoms of the heterocycloalkylene.

The term "pyrolytic carbon" refers to carbon formed by pyrolysis. Pyrolytic carbon may comprise hard carbon and/or soft carbon, but does not include graphite.

The term "optionally substituted" is used herein to indicate a moiety that can be unsubstituted or substituted by one or more substituent. When a moiety term is used without specifically indicating as substituted, the moiety is unsubstituted.

Energy Storage Device

An energy storage device includes a first electrode, a second electrode, a separator between the first electrode and the second electrode, and an electrolyte in contact with the first electrode, the second electrode, and the separator. The electrolyte serves to facilitate ionic transport between the first electrode and the second electrode. One of the first electrode and the second electrode is an anode (i.e., negative electrode), and the other is a cathode (i.e., positive electrode). In some embodiments, energy storage devices may include batteries, capacitors, and battery-capacitor hybrids.

In some implementations, at least one electrode may be a Si-based electrode. The Si-based electrode may be the anode. In some embodiments, the Si-based anode includes silicon in an amount of about 25% or more of the active material used in the electrode. In some embodiments, the Si-based anode is a Si-dominant anode, where silicon is the majority (e.g., in an amount greater than about 50%) of the active material used in the electrode.

The electrochemical behaviors of Si-based electrodes are strongly dependent on the electrolyte systems, which exert considerably influence not only on cell safety and kinetics but also on the interfacial property including the quality of SEI layer. The properties of electrolyte formulations, including Li-containing salt, solvents, additives, etc., are important factors that affect cell energy storage, cycle performance and rate capability (powder density, fast charging ability), etc. To overcome the current obstacles associated with developing high-energy full-cells with Si-based anodes, the next generation of oxidation-stable electrolytes and/or electrolyte additives are developed. The electrolyte or electrolyte additives can form a stable, electronically insulating but ionically conducting SEI layer on the surface of Si anodes. Additionally, these electrolytes or additives may also help modify cathode surfaces, forming stable CEI layers. These could enable the electrochemical stability of Li-ion batteries when cycled at higher voltages and help with calendar life of the batteries. In addition, to alleviate battery safety concerns, these additives may impart an increased thermal stability to the organic components of the electrolyte, drive a rise in the flash point of the electrolyte formulations, increase the flame-retardant effectiveness and enhance thermal stability of SEI or CEI layers on the surface of electrodes.

Electrolyte System

A Li-ion battery includes a first electrode, a second electrode, a separator between the first electrode and the second electrode, and an electrolyte in contact with the first electrode, the second electrode, and the separator. The electrolyte serves to facilitate ionic transport between the first electrode and the second electrode. In some embodiments, the first electrode and the second electrode can refer to anode and cathode or cathode and anode, respectively. An electrolyte for a Li-ion battery can include at least a solvent and a Li ion source, such as a Li-containing salt. The composition of the electrolyte may be selected to provide a Li-ion battery with improved performance. For example, the electrolyte may further contain one or more additional component(s) such as electrolyte additive(s) and/or co-solvent(s).

As disclosed herein, the electrolyte for a Li-ion battery may include a solvent comprising a cyclic carbonate and/or a linear carbonate. In some implementations, the cyclic carbonate is a fluorine-containing cyclic carbonate. Examples of the cyclic carbonate include fluoroethylene carbonate (FEC), di-fluoroethylene carbonate (DiFEC), tri-fluoropropylene carbonate (TFPC), ethylene carbonate (EC), vinyl carbonate (VC), and propylene carbonate (PC), 4-fluoromethyl-5-methyl-1,3-dioxolan-2-one (F-t-BC), 3,3-difluoropropylene carbonate (DFPC), 3,3,4,4,5,5,6,6,6-Nonafluorohexyl-1-ene carbonate, etc. Examples of the linear carbonate include ethyl methyl carbonate (EMC), dimethyl carbonate (DMC), and diethyl carbonate (DEC), and some partially or fully fluorinated ones.

In some implementations, the electrolyte can include more than one solvent. For example, the electrolyte may include two or more co-solvents. In some embodiments, at least one of the co-solvents in the electrolyte is a fluorine-containing compound, such as a fluorine-containing cyclic carbonate, a fluorine-containing linear carbonate, and/or a fluoroether. Examples of fluorine-containing compound may include FEC, DiFEC, TFPC, F-t-PC, DFPC, 1,1,2,2-tetrafluoroethyl 2,2,3,3-tetrafluoropropyl ether, 3,3,4,4,5,5,6,6,6-Nonafluorohexyl-1-ene carbonate, and other partially or fully fluorinated linear carbonates, partially or fully fluorinated cyclic carbonates, and partially or fully fluorinated ethers, etc. In some embodiments, the electrolyte contains FEC. In some embodiments, the electrolyte contains both EMC and FEC. In some embodiments, the electrolyte is free or substantially free of non-fluorine-containing cyclic carbonates, such as EC, VC, and PC. In some implementations, the electrolyte may further contain other co-solvent(s), such as methyl acetate (MA), ethyl acetate (EA), methyl propanoate, and gamma butyrolactone (GBL). The cyclic carbonates may be beneficial for SEI layer formations, while the linear carbonates may be helpful for dissolving Li-containing salt and for Li-ion transport.

An additional component in the electrolyte may be an additive or a co-solvent. As used herein, an additive of the electrolyte refers to a component that makes up less than 10% by weight (wt %) of the electrolyte. In some embodiments, the amount of each additive in the electrolyte may be from about 0.2 wt % to about 1 wt %, 0.1 wt % to about 2 wt %, 0.2 wt % to about 9 wt %, from about 0.5 wt % to about 9 wt %, from about 1 wt % to about 9 wt %, from about 1 wt % to about 8 wt %, from about 1 wt % to about 8 wt %, from about 1 wt % to about 7 wt %, from about 1 wt % to about 6 wt %, from about 1 wt % to about 5 wt %, from about 2 wt % to about 5 wt %, or any value in between. For ecample, the total amount of the additive(s) may be from about 1 wt % to about 9 wt %, from about 1 wt % to about 8 wt %, from about 1 wt % to about 7 wt %, from about 2 wt % to about 7 wt %, or any value in between.

As used herein, a co-solvent of an electrolyte has a concentration of at least about 10% by weight (wt %). In some embodiments, a co-solvent of the electrolyte may be about 20%, about 40%, about 60%, or about 80%, or about 90% by weight of the electrolyte. In some embodiments, a co-solvent may have a concentration from about 10% to about 90%, from about 10% to about 80%, from about 10% to about 60%, from about 20% to about 60%, from about 20% to about 50%, from about 30% to about 60%, or from about 30% to about 50% by weight.

In the present disclosure, cyanate based compound is used as an additional co-solvent or an additive in the electrolyte system for energy storage devices with Si-based anodes. When used as a co-solvent or an additive, the cyanate based compound can stabilize solid/electrolyte interface film to reduce electrolyte reactions (e.g., oxidation on the NCM, NCA, or LCO cathode and reduction on the Si-based anode), reduce Si-based anode volume expansion, and protect transition metal ion dissolution from NCM or NCA cathode and stabilize the subsequent structure changes. Such co-solvent/additive can also avoid the exothermic reaction between the released oxygen for LCO and organic electrolyte and enhance the thermal stability of LCO cathode. Furthermore, such co-solvent/additive can reduce the flammability and enhance the thermal stability of organic electrolytes and increase the safety of electrolyte solutions. Due to their versatility in reaction chemistry and overall stability in electrochemical environments, as well as have excellent flame resistance or fire retardant properties, adding cyanate based compound into electrolyte solutions may help improve both overall electrochemical performance and safety of Si anode-based Li-ion batteries.

An electrolyte system including a cyanate based compound, a linear carbonate, a cyclic carbonate, and a Li-containing salt is disclosed. The cyanate based compound includes a compound having at least one of formulae (I), (II), (III), (IV), (V), (VI), (VII) and (VIII) shown below:

$$R^1-N=C=O; \quad (I)$$

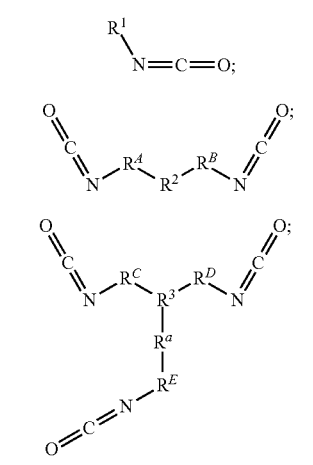

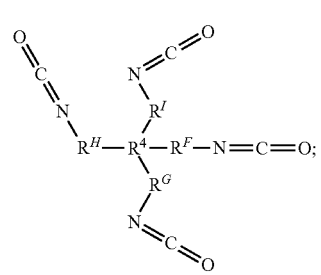

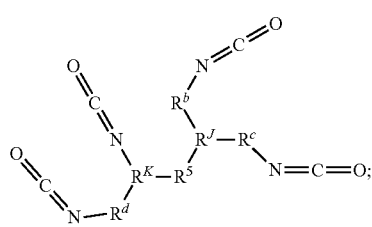

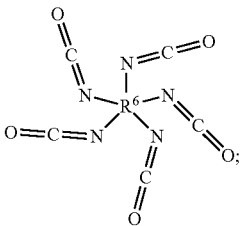

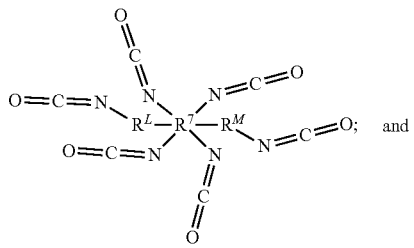

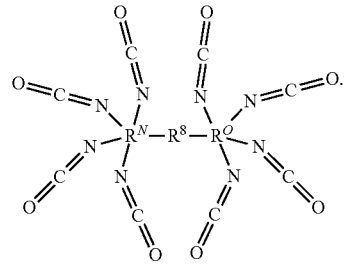

In some embodiments, $R^1$ is selected from the group consisting of a $C_1$-$C_8$ alkyl, a $C_2$-$C_8$ alkenyl, a $C_2$-$C_8$ alkynyl, a cycloalkyl, an aryl, a heteroalkenyl,

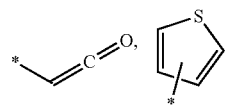

and

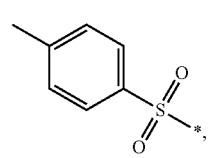

wherein $R^1$ may be optionally substituted by —F, alkyl, alkenyl, cycloalkyl, aryl, —CN, —N$^+$C$^-$, fluoro-alkyl, fluoro-ether, —N(CH$_3$)$_2$,

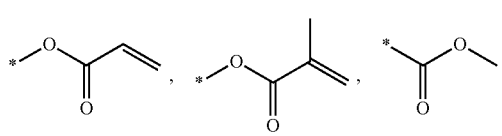

and

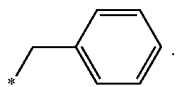 [SMILES: *Cc1ccccc1]

In some embodiments, $R^2$, $R^3$, $R^4$, $R^5$, $R^6$, $R^7$ and $R^8$ are each independently selected from the group consisting of a $C_1$-$C_8$ alkylene, a $C_2$-$C_8$ alkenylene, a $C_2$-$C_8$ alkynylene, a cycloalkylene, an arylene, —O—,

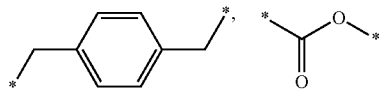

and

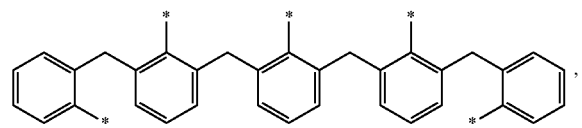

wherein $R^2$, $R^3$, $R^4$, $R^5$, $R^6$, $R^7$ and $R^9$ may be optionally substituted by —F, alkyl, alkenyl, cycloalkyl, aryl, —CN, —N$^+$C—, fluoro-alkyl, fluoro-ether, —N(CH$_3$)$_2$,

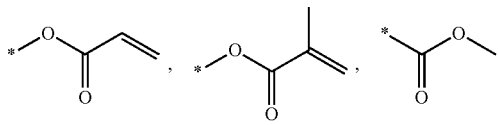

and

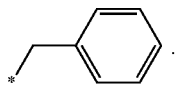

In some embodiments, $R^A$, $R^B$, $R^C$, $R^D$, $R^E$, $R^F$, $R^G$, $R^H$, $R^I$, $R^J$, $R^K$, $R^L$, $R^M$, $R^N$ and $R^O$ are each independently selected from the group consisting of a bond, a $C_1$-$C_8$ alkylene, a cycloalkylene, an arylene and —Si—, wherein $R^A$, $R^B$, $R^C$, $R^D$, $R^E$, $R^F$, $R^G$, $R^H$, $R^I$, $R^J$, $R^K$, $R^L$, $R^M$, $R^N$ and $R^O$ may be optionally substituted by —F, alkyl, alkenyl, alkynyl and aryl.

In some embodiments, $R^a$, $R^b$, $R^c$ and $R^d$ are each independently selected from the group consisting of a bond, a $C_1$-$C_8$ alkylene, a $C_2$-$C_8$ alkenylene, a $C_2$-$C_8$ alkynylene, and

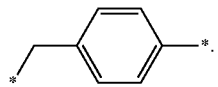

In some implementations, the cyanate based compound is selected from allyl isocyanate; vinyl isocyanate; 1-isocyanatoprop-1-ene; (E)-1-isocyanatoprop-1-ene; 4-isocyanatobut-1-ene; 1-isocyanato-2-methylprop-1-ene; 1-isocyanato-3-methylbut-2-ene; 3-isocyanatobut-1-ene; 3-isocyanato-3-methylbut-1-ene; Isocyanatosulfanylethene; 3-isocyanatosulfanylprop-1-ene; Isocyanatooxyethene; 3-isocyanatoprop-1-yne; 3-isocyanato-3-methylbut-1-yne; 4-isocyanatobut-1-yne; 1-fluoro-2-isocyanatocyclopropane; Isocyanatomethylcyclopropane; (1S, 2R)-1-fluoro-2-isocyanatocyclopropane; 1-fluoro-2-isocyanatoethane; 1-isocyanatopropa-1,2-diene; (1Z)-1-isocyanatobuta-1,3-diene; 2-isocyanatoethenone; 6-isocyanatohexanenitrile; 6-isocyanatohexyl cyanate; 2,4-difluoro-1,6-diisocyanatohexane; 3,3,4,4-tetrafluoro-1,6-diisocyanatohexane; Thien-2-yl isocyanate; Thien-3-yl isocyanate; 2-Methacryloyloxyethyl isocyanate (CAS: 30674-80-7); 1-Isocyanatoethyl methacrylate; 2-Isocyanatoethyl Acrylate (CAS: 13641-96-8); Phenyl isocyanate; 4-(Trifluoromethoxy)phenyl isocyanate; 4-(Trifluoromethyl)phenyl isocyanate; 3,5-Bis(trifluoromethyl)phenyl isocyanate; 2-Fluoro-1-isocyanato-3-(trifluoromethyl)benzene; 1-(Difluoromethoxy)-4-isocyanatobenzene; 4-isocyanato-N,N-dimethylaniline; 4-methylbenzene-1-sulfonyl isocyanate; 1-isocyanato-2-phenylbenzene; 1-isocyanato-4-phenylbenzene; 1-ethenyl-4-isocyanatobenzene; 1-isocyanato-4-prop-2-enylbenzene; 1-isocyanato-4-prop-1-en-2-ylbenzene; 1-cyclopentyl-4-isocyanatobenzene; 1-cyclopropyl-4-isocyanatobenzene; 1-isocyanato-4-[(4-isocyanophenyl)methyl]benzene; Diisocyanatomethane; 1,2-diisocyanatoethane; 1,3-diisocyanatopropane; 2-fluoro-1,3-diisocyanatopropane; 1,4-diisocyanatobutane; 1,5-pentane diisocyanate; 1,6-diisocyanatohexane; 1,6-Diisocyanato-2-methylhexane; methyl 2,6-diisocyanatohexanoate; Isophorone diisocyanate; 2,3-diisocyanato-7-methylbicyclo[2.2.1]heptane; 4,4'-diisocyanatodicyclohexylmethane; TCD-diisocyanate (28807-72-9); 1,2-Diisocyanatobenzene; 1,3-Phenylene diisocyanate; 1,4-Diisocyanatobenzene; Toluene diisocyanate; Tetramethylxylene diisocyanate; 1-isocyanato-4-(2-isocyanatopropan-2-yl)benzene; 1-isocyanato-4-(4-isocyanatophenyl)benzene; 1-isocyanato-3-(4-isocyanatophenyl)benzene; 1-isocyanato-4-(4-isocyanato-3-methylphenyl)-2-methylbenzene; 1-isocyanato-4-(4-isocyanatocyclohexyl)benzene; 1-isocyanato-4-[(4-isocyanatophenyl)methyl]benzene; 1-isocyanato-2-[(4-isocyanatophenyl)methyl]benzene; 1-isocyanato-3-[(3-isocyanatophenyl)methyl]benzene; 1-isocyanato-4-[(4-isocyanatocyclohexyl)methyl]benzene; 1-isocyanato-4-[(4-isocyanatophenyl)methyl]-2-methylbenzene; 1-isocyanato-4-[(4-isocyanato-3-methylphenyl)methyl]-2-methylbenzene; 4-isocyanato-2-[(4-isocyanatophenyl)methyl]-1-methylbenzene; 1-isocyanato-2-[(2-isocyanatophenyl)methyl]benzene; 4-isocyanato-1-(4-isocyanato-2-methylphenyl)-2-methylbenzene; 1-isocyanato-4-[1-(4-isocyanatophenyl)ethyl]benzene; 1-isocyanato-4-[2-(4-isocyanatophenyl)propan-2-yl]benzene; 1,4-bis(4-isocyanatophenyl)benzene; 1,4-bis[(4-isocyanatophenyl)methyl]benzene; 1-isocyanato-4-[1-(4-isocyanatophenyl)ethenyl]benzene; 1-isocyanato-2-[(E)-2-(4-isocyanatophenyl)ethenyl]benzene; 1-isocyanato-4-[(E)-2-(4-isocyanatophenyl)ethenyl]benzene; 1-isocyanato-4-[(E)-1-(4-isocyanatophenyl)prop-1-en-2-yl]benzene; (Z)-2,3-bis(4-isocyanatophenyl)prop-2-enenitrile; 1-isocyanato-4-[2-(4-isocyanatophenyl)ethynyl]benzene; 1-isocyanato-4-[1,1,2,2-tetrafluoro-2-(4-isocyanatophenyl)ethyl]benzene; 1-isocyanato-4-[1-(4-isocyanatophenyl)cyclopropyl]benzene; 1-[cyclohexyl-(4-isocyanatophenyl)methyl]-4-isocyanatobenzene; 2-isocyanato-5-[(4-isocyanatophenyl)methyl]-1,3-bis(prop-2-enyl)benzene; 1-isocyanato-2-(2-isocyanato-5-prop-2-enylphenyl)-4-prop-2-enylbenzene; 1,1,2-triisocyanatoethane; 1,1,3-triisocyanatopropane; 1,1,5-triisocyanatopentane; 1,2,6-triisocyanatohexane; 1,3,6- triisocyanatohexane; 1,4,7-triisocyanatoheptane; 1,1,6-triisocyanatohexane; 2-isocyanatoethyl (2S)-2,6-diisocyanatohexanoate; 2-isocyanatoethyl 2,6-diisocyanatohexanoate; 4-isocyanatobutyl 2,6-diisocyanatohexanoate; 1-[diisocyanato(phenyl)methyl]-2-isocyanatobenzene; 2,4-diisocyanato-1-[(4-isocyanatophenyl)methyl]benzene; 1,4-diisocyanato-2-[(4-isocyanatophenyl)methyl]benzene; 1-isocyanato-4-[isocyanato-(4-isocyanatophenyl)methyl]benzene; 1-[bis(4-isocyanatophenyl)methyl]-4-isocyanatobenzene; 1-[1,3-bis(4-isocyanatophenyl)propan-2-yl]-4-isocyanatobenzene; 2-benzyl-1,3,5-triisocyanatobenzene; 2,4-diisocyanato-1-[(4-isocyanatophenyl)-phenylmethyl]benzene; 1,1,1,5-tetraisocyanatohexane; 1,1,1,6-tetraisocyanatohexane; 1,1,6,6-tetraisocyanatohexane; 1-[diisocyanato-(4-isocyanatophenyl)methyl]-4-isocyanatobenzene; 4,4'-Benzylidenebis(6-methyl-m-phenylene) tetraisocyanate; 1,5-diisocyanato-2-[[4-isocyanato-3-[(4-isocyanatophenyl)methyl]phenyl]methyl]-4-methylbenzene; 1-(1,3-diisocyanato-3,3-diphenylpropyl)-2,4-diisocyanato-5-propan-2-yl-benzene; 1-[(3,5-diisocyanato-2-methylphenyl)-phenylmethyl]-3,5-diisocyanato-2-methylbenzene; 5-[bis(4-isocyanatophenyl)methyl]-1,3-diisocyanato-2-methylbenzene; 2,6-Bis(2-isocyanato-3-((2-isocyanatophenyl)methyl)benzyl)phenyl isocyanate; [diisocyanato(phenyl)silyl]oxy-diisocyanato-phenylsilane; 2-[diisocyanato(phenyl)silyl]ethyl-diisocyanato-phenylsilane; 1-isocyanato-4-[1,1,3,3-tetraisocyanato-3-(4-isocyanatophenyl)propyl]benzene; and 4,4'-benzylidenebis(6-methyl-m-phenylene) tetraisocyanate, or combinations thereof.

Example structures of cyanate based compounds are shown below:

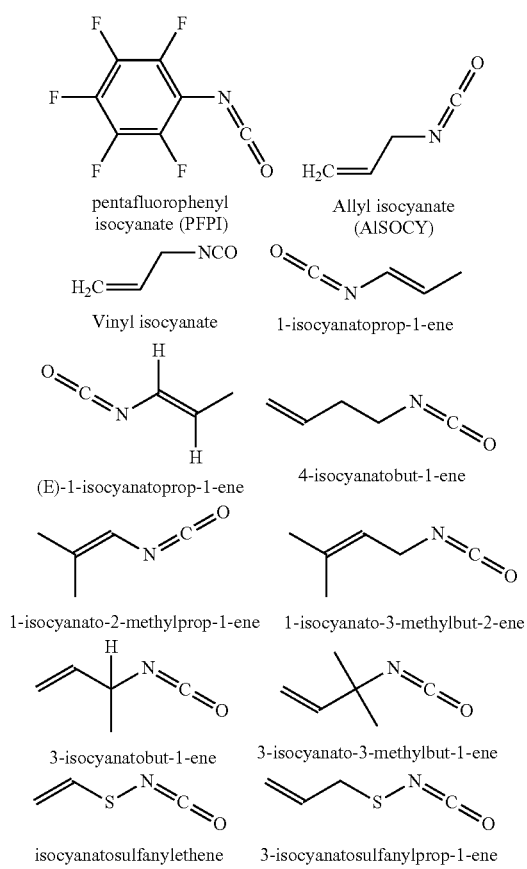

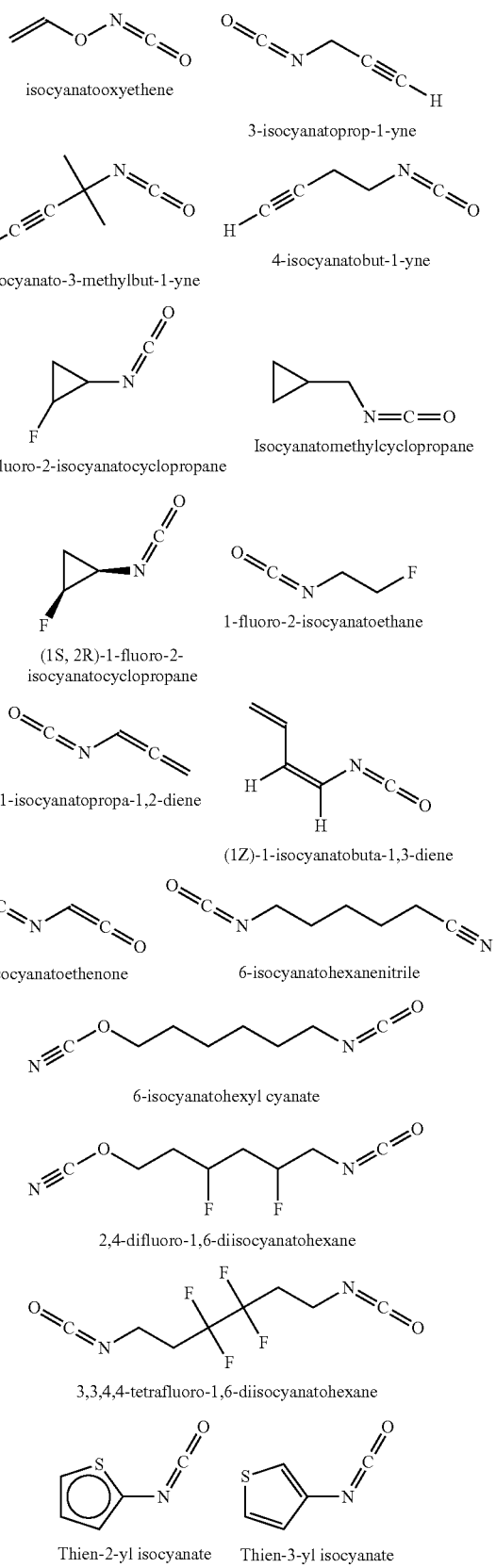

-continued

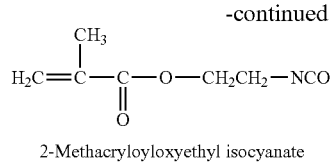
2-Methacryloyloxyethyl isocyanate

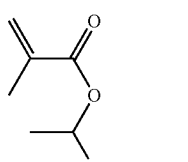
1-Isocyanatoethyl methacrylate

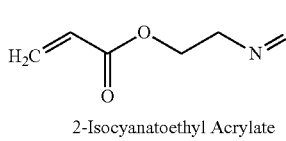
2-Isocyanatoethyl Acrylate

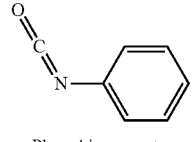
Phenyl isocyanate

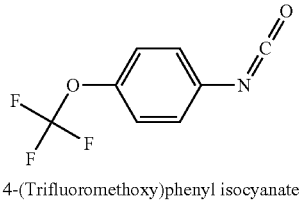
4-(Trifluoromethoxy)phenyl isocyanate

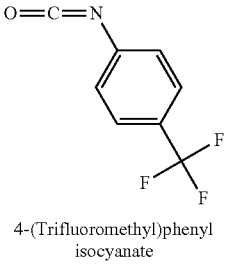
4-(Trifluoromethyl)phenyl isocyanate

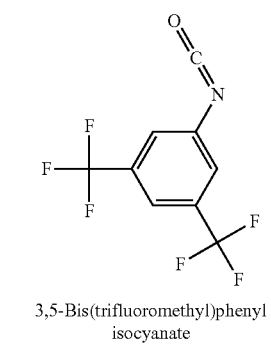
3,5-Bis(trifluoromethyl)phenyl isocyanate

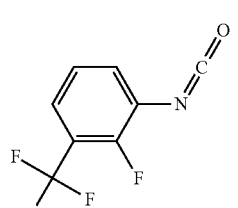
2-Fluoro-1-isocyanato-3-(trifluoromethyl)benzene

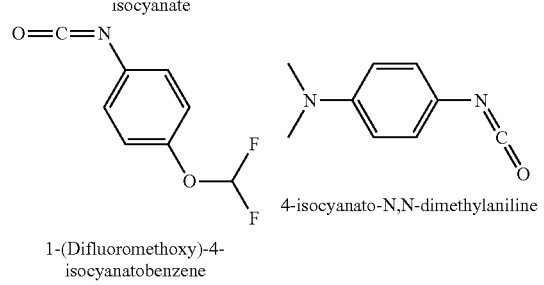

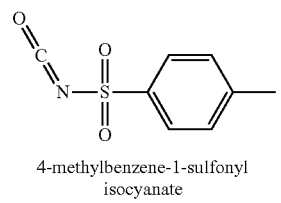
1-(Difluoromethoxy)-4-isocyanatobenzene 4-isocyanato-N,N-dimethylaniline

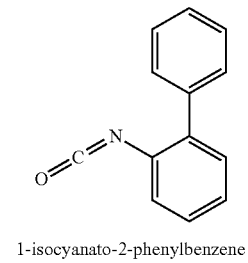
4-methylbenzene-1-sulfonyl isocyanate 1-isocyanato-2-phenylbenzene

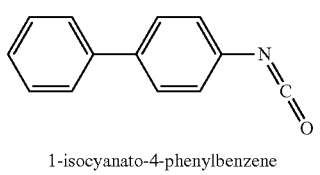
1-isocyanato-4-phenylbenzene

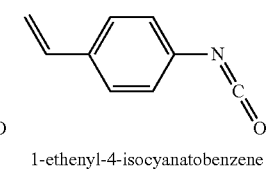
1-ethenyl-4-isocyanatobenzene

-continued

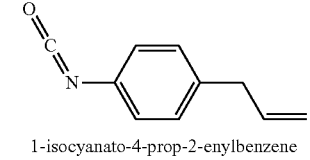
1-isocyanato-4-prop-2-enylbenzene

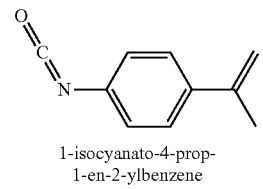
1-isocyanato-4-prop-1-en-2-ylbenzene

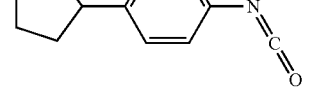
1-cyclopentyl-4-isocyanatobenzene

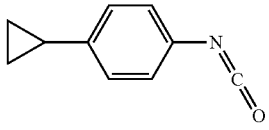
1-cyclopropyl-4-isocyanatobenzene

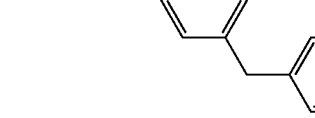
1-isocyanato-4-[(4-isocyanatophenyl)methyl]benzene

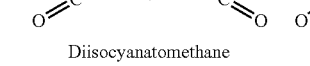
Diisocyanatomethane

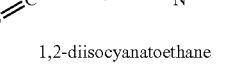
1,2-diisocyanatoethane

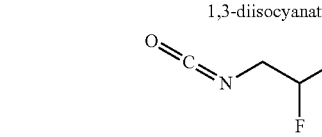
1,3-diisocyanatopropane

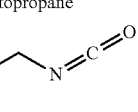
2-fluoro-1,3-diisocyanatopropane

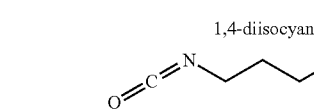
1,4-diisocyanatobutane

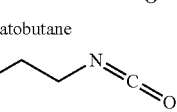
1,5-pentane diisocyanate

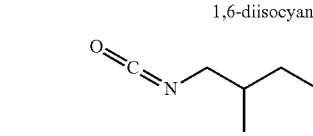
1,6-diisocyanatohexane

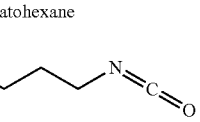
1,6-Diisocyanato-2-methylhexane

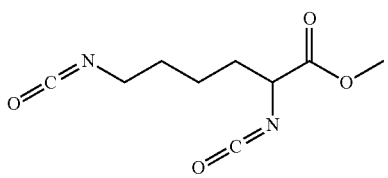
methyl 2,6-diisocyanatohexanoate

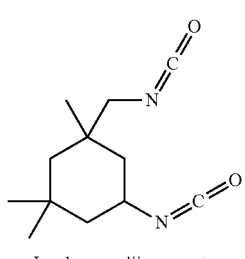
Isophorone diisocyanate

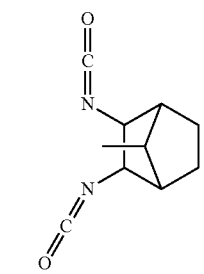
2,3-diisocyanato-7-methylbicyclo[2.2.1]heptane

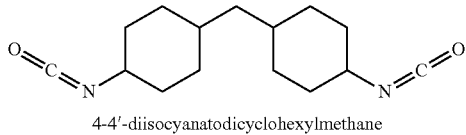
4-4′-diisocyanatodicyclohexylmethane

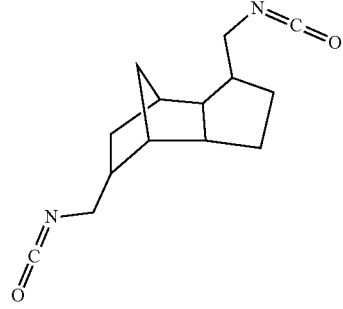
TCD-diisocyanate

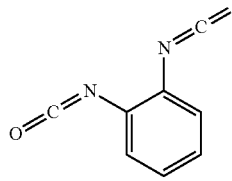
1,2-Diisocyanatobenzene

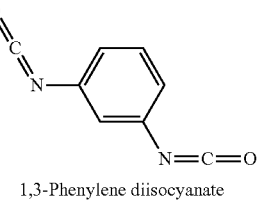
1,3-Phenylene diisocyanate

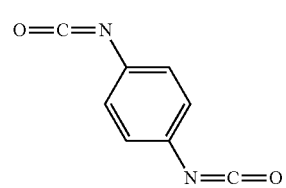
1,4-Diisocyanatobenzene

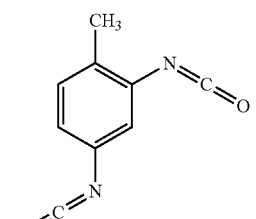
Toluene diisocyanate

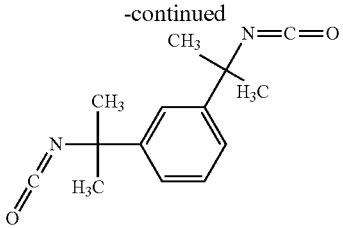
Tetramethylxylene diisocyanate

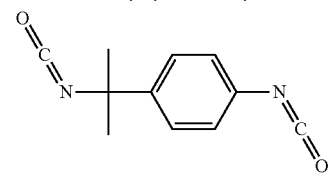
1-isocyanato-4-(2-isocyanatopropan-2-yl)benzene

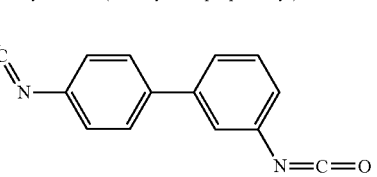
1-isocyanato-3-(4-isocyanatophenyl)benzene

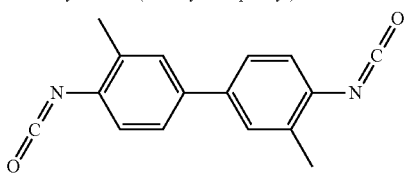
1-isocyanato-4-(4-isocyanato-3-methylphenyl)-2-methylbenzene

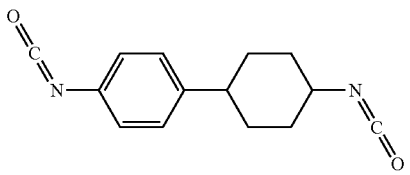
1-isocyanato-4-(4-isocyanatocyclohexyl)benzene

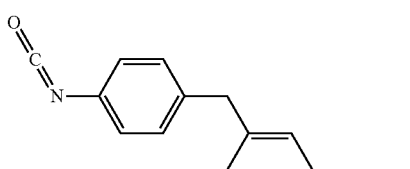
1-isocyanato-4-[(4-isocyanatophenyl)methyl]benzene

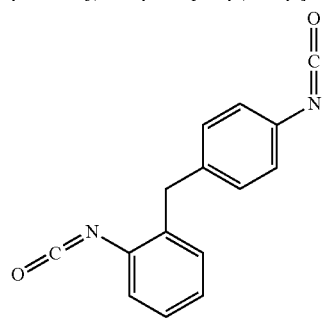
1-isocyanato-2-[(4-isocyanatophenyl)methyl]benzene

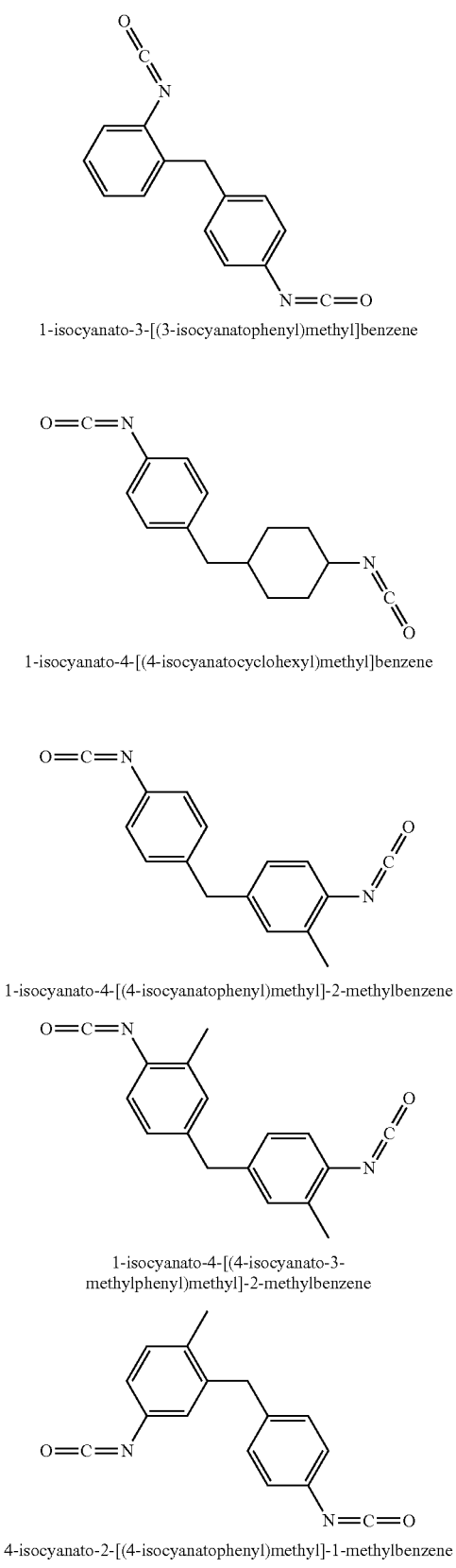

1-isocyanato-3-[(3-isocyanatophenyl)methyl]benzene 1-isocyanato-4-[(4-isocyanatocyclohexyl)methyl]benzene 1-isocyanato-4-[(4-isocyanatophenyl)methyl]-2-methylbenzene 1-isocyanato-4-[(4-isocyanato-3-methylphenyl)methyl]-2-methylbenzene 4-isocyanato-2-[(4-isocyanatophenyl)methyl]-1-methylbenzene

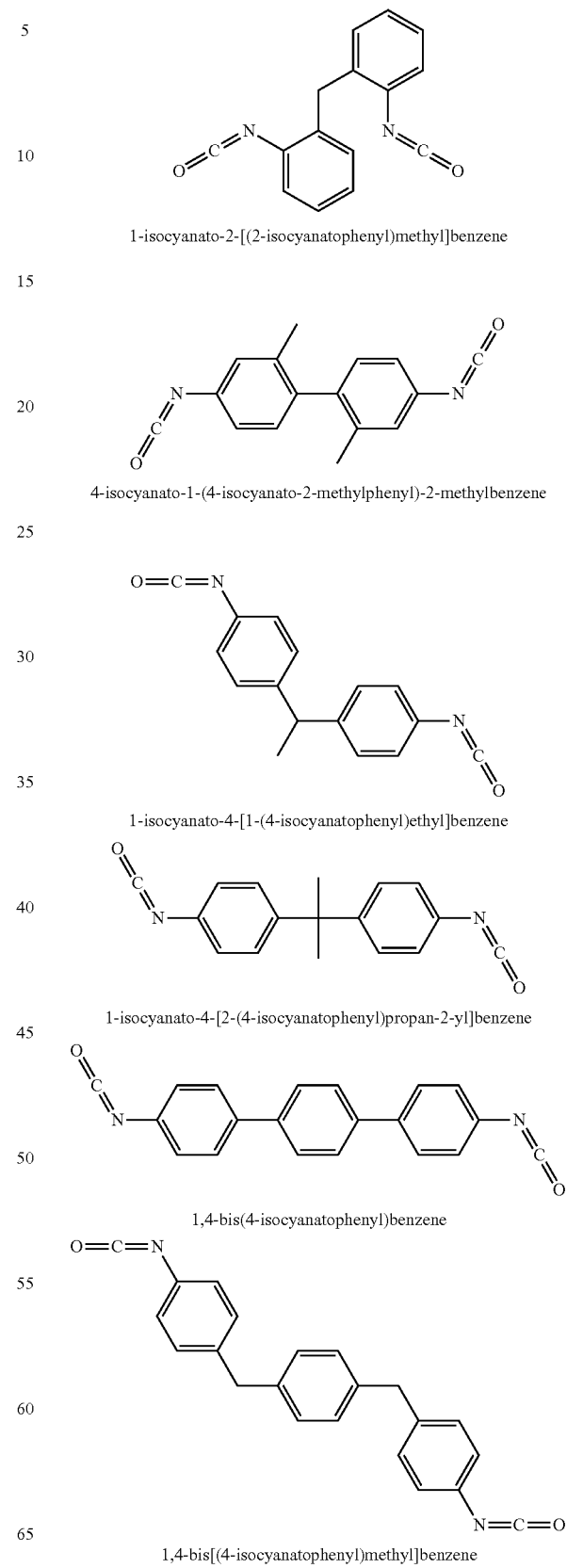

1-isocyanato-2-[(2-isocyanatophenyl)methyl]benzene 4-isocyanato-1-(4-isocyanato-2-methylphenyl)-2-methylbenzene 1-isocyanato-4-[1-(4-isocyanatophenyl)ethyl]benzene 1-isocyanato-4-[2-(4-isocyanatophenyl)propan-2-yl]benzene 1,4-bis(4-isocyanatophenyl)benzene 1,4-bis[(4-isocyanatophenyl)methyl]benzene

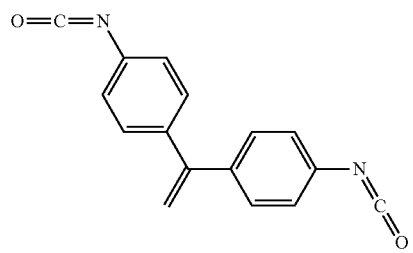

1-isocyanato-4-[1-(4-isocyanatophenyl)ethenyl]benzene

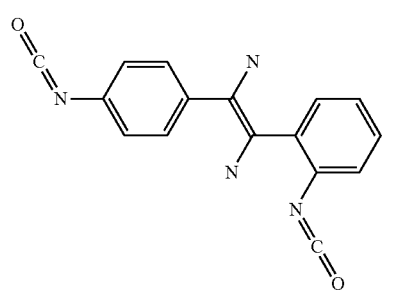

1-isocyanato-2-[(E)-2-(4-isocyanatophenyl)ethenyl]benzene

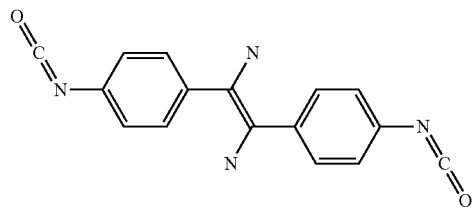

1-isocyanato-4-[(E)-2-(4-isocyanatophenyl)ethenyl]benzene

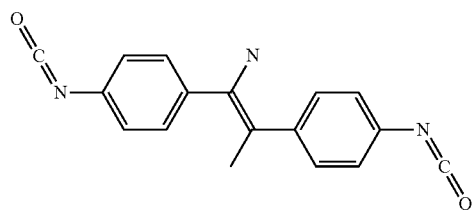

1-isocyanato-4-[(E)-1-(4-isocyanatophenyl)prop-1-en-2-yl]benzene

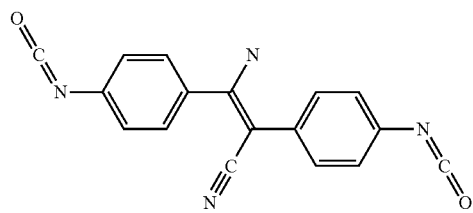

(Z)-2,3-bis(4-isocyanatophenyl)prop-2-enenitrile

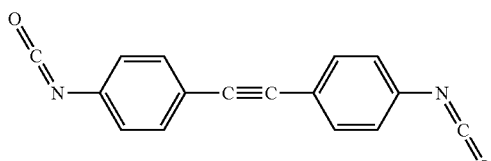

1-isocyanato-4-[2-(4-isocyanatophenyl)ethynyl]benzene

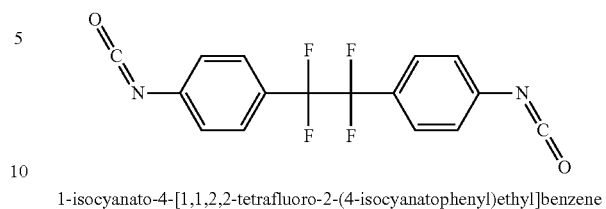

1-isocyanato-4-[1,1,2,2-tetrafluoro-2-(4-isocyanatophenyl)ethyl]benzene

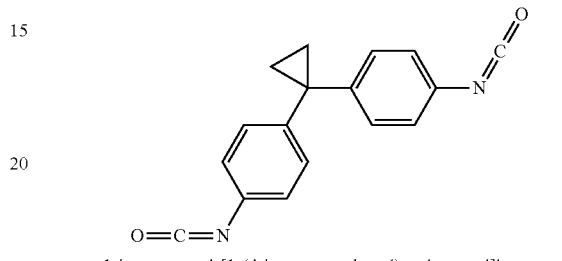

1-isocyanato-4-[1-(4-isocyanatophenyl)cyclopropyl]benzene

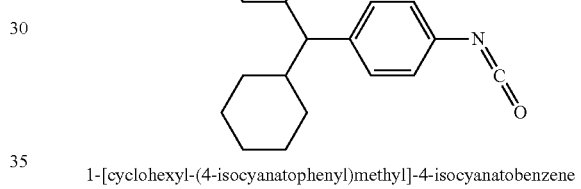

1-[cyclohexyl-(4-isocyanatophenyl)methyl]-4-isocyanatobenzene

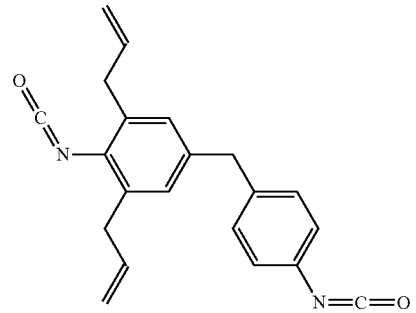

2-isocyanato-5-[(4-isocyanatophenyl)methyl]-1,3-bis(prop-2-enyl)benzene
t

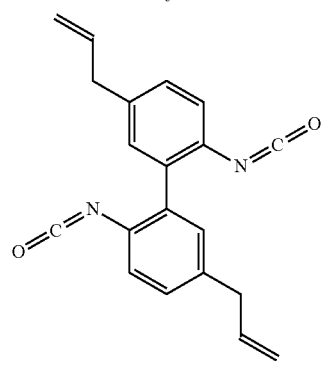

1-isocyanato-2-(2-isocyanato-5-prop-2-enyphenyl)-4-prop-2-enylbenzene

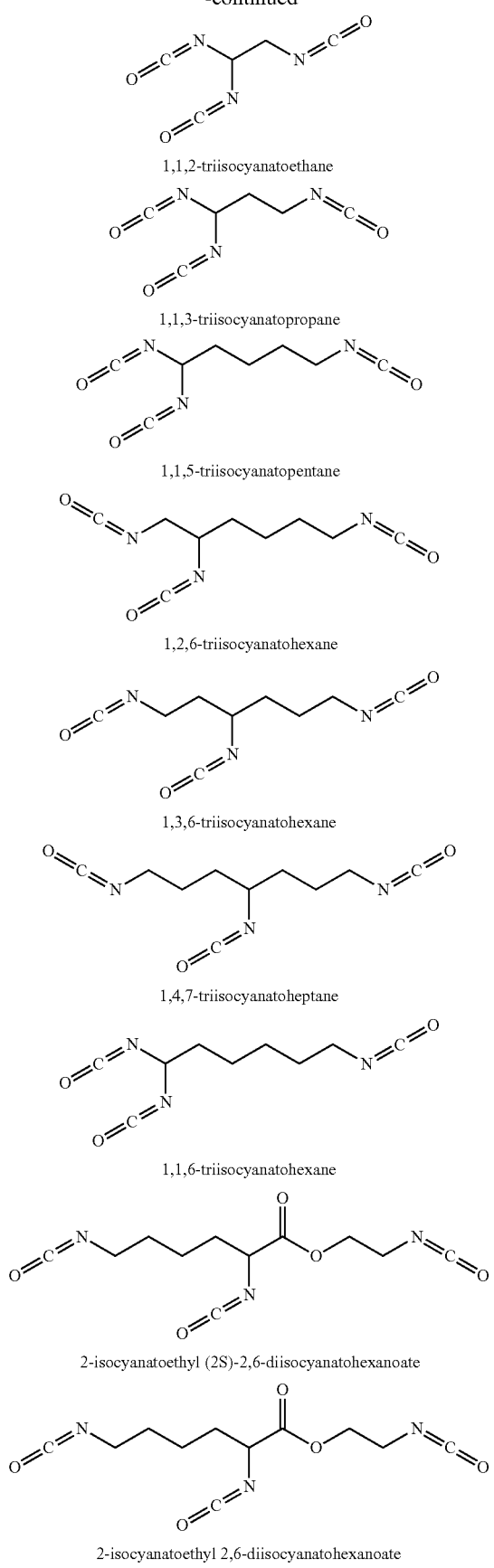

1,1,2-triisocyanatoethane 1,1,3-triisocyanatopropane 1,1,5-triisocyanatopentane 1,2,6-triisocyanatohexane 1,3,6-triisocyanatohexane 1,4,7-triisocyanatoheptane 1,1,6-triisocyanatohexane 2-isocyanatoethyl (2S)-2,6-diisocyanatohexanoate 2-isocyanatoethyl 2,6-diisocyanatohexanoate

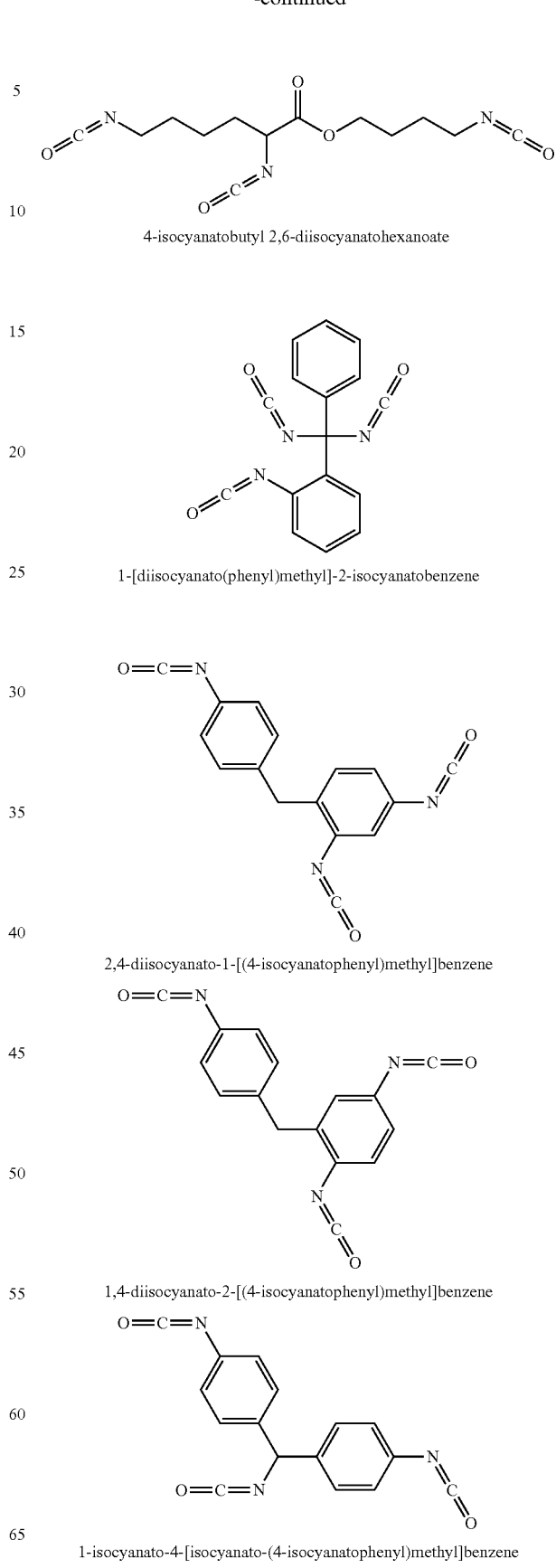

4-isocyanatobutyl 2,6-diisocyanatohexanoate

1-[diisocyanato(phenyl)methyl]-2-isocyanatobenzene 2,4-diisocyanato-1-[(4-isocyanatophenyl)methyl]benzene 1,4-diisocyanato-2-[(4-isocyanatophenyl)methyl]benzene 1-isocyanato-4-[isocyanato-(4-isocyanatophenyl)methyl]benzene

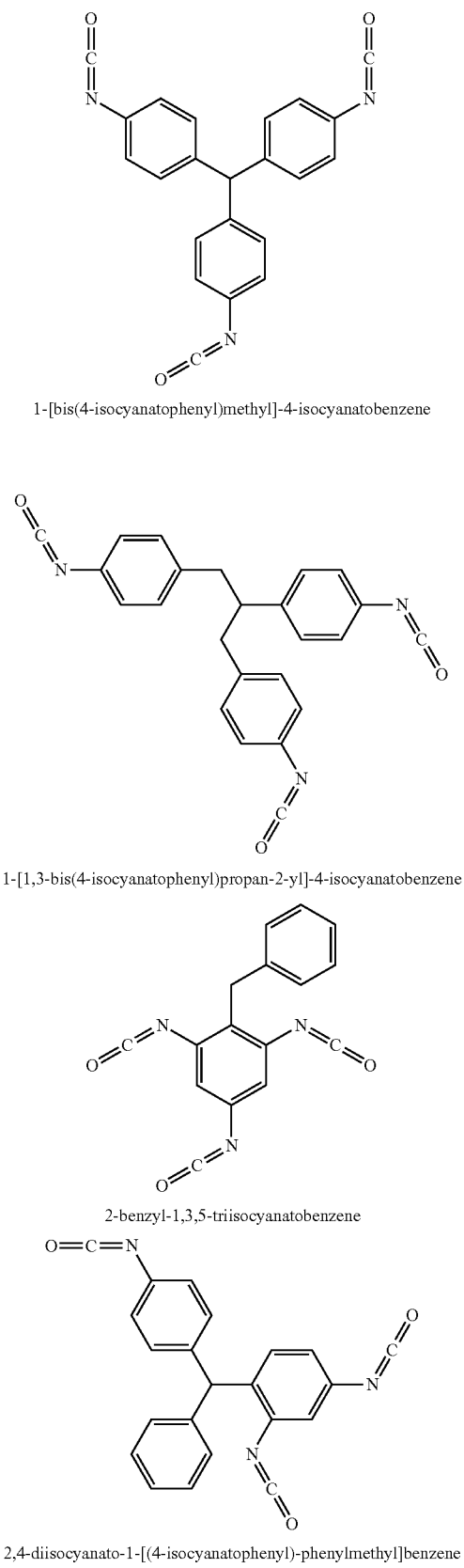

1-[bis(4-isocyanatophenyl)methyl]-4-isocyanatobenzene

1-[1,3-bis(4-isocyanatophenyl)propan-2-yl]-4-isocyanatobenzene 2-benzyl-1,3,5-triisocyanatobenzene 2,4-diisocyanato-1-[(4-isocyanatophenyl)-phenylmethyl]benzene

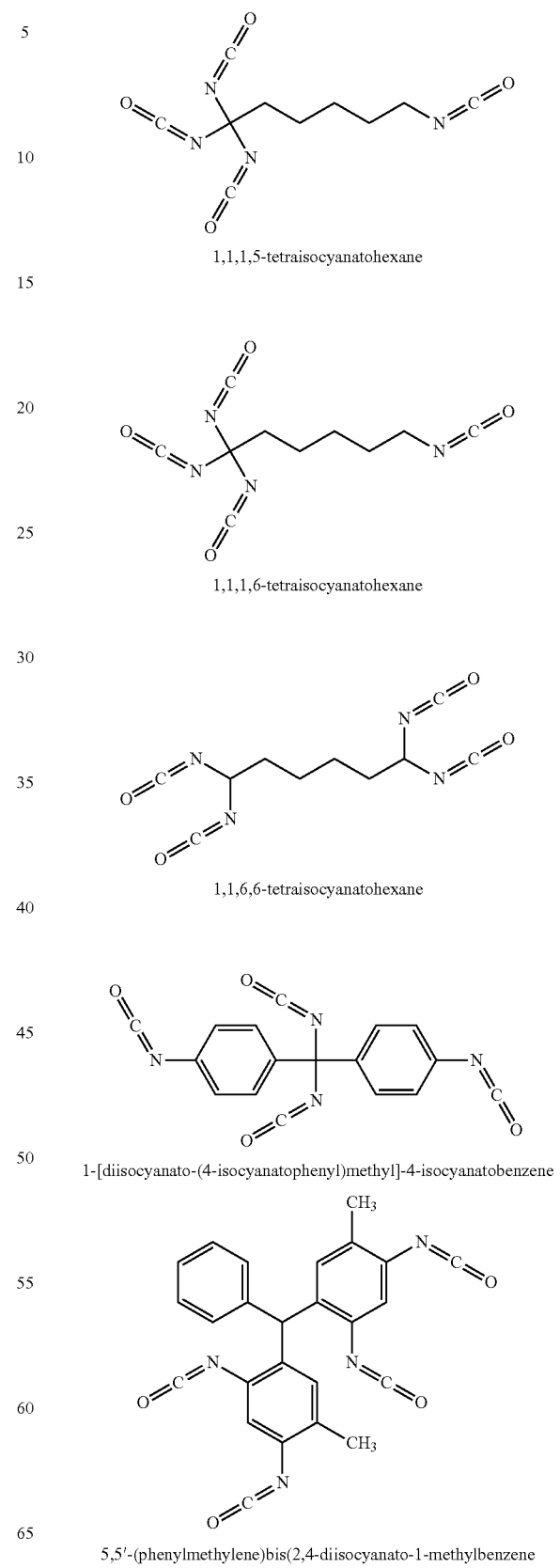

1,1,1,5-tetraisocyanatohexane 1,1,1,6-tetraisocyanatohexane 1,1,6,6-tetraisocyanatohexane 1-[diisocyanato-(4-isocyanatophenyl)methyl]-4-isocyanatobenzene 5,5'-(phenylmethylene)bis(2,4-diisocyanato-1-methylbenzene)

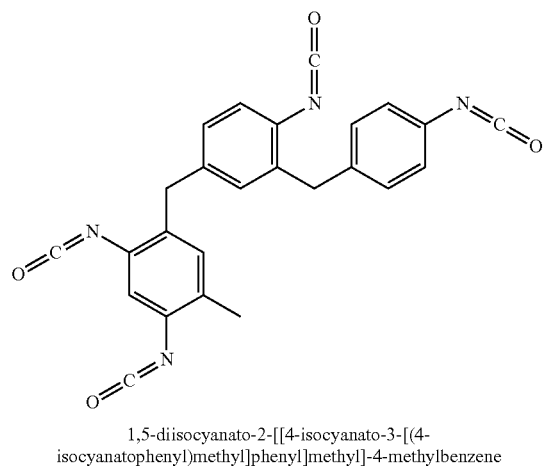

1,5-diisocyanato-2-[[4-isocyanato-3-[(4-isocyanatophenyl)methyl]phenyl]methyl]-4-methylbenzene

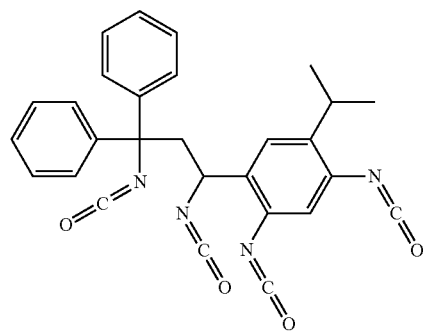

1-(1,3-diisocyanato-3,3-diphenylpropyl)-2,4-diisocyanato-5-propan-2-ylbenzene

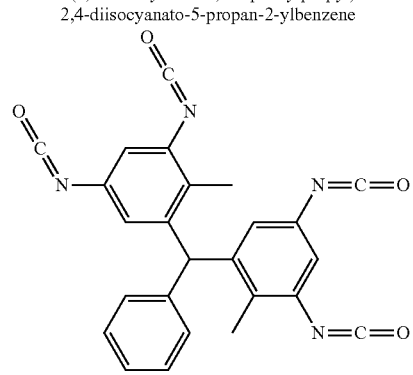

1-[(3,5-diisocyanato-2-methylphenyl)-phenylmethyl]-3,5-diisocyanato-2-methylbenzene

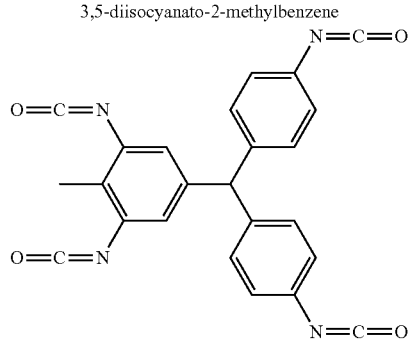

5-[bis(4-isocyanatophenyl)methyl]-1,3-diisocyanato-2-methylbenzene

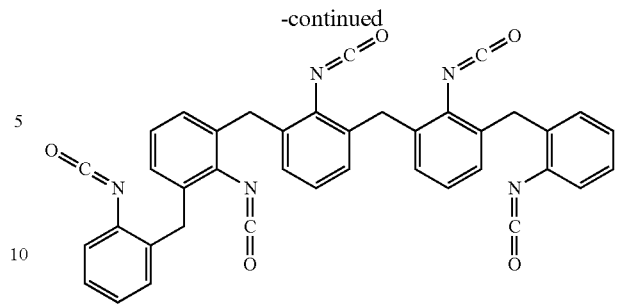

2,6-Bis(2-isocyanato-3-((2-isocyanatophenyl)methyl)benzyl)phenylisocyanate

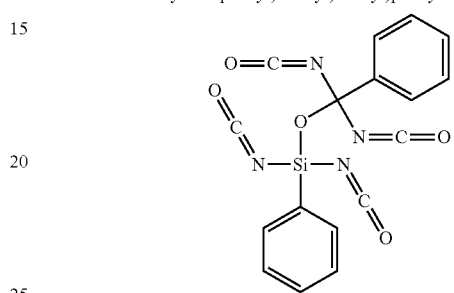

[diisocyanato(phenyl)silyl]oxy-diisocyanato-phenylsilane

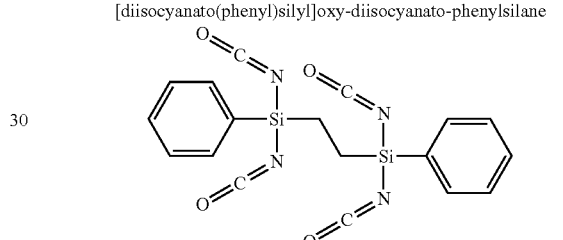

2-[diisocyanato(phenyl)silyl]ethyl-diisocyanato-phenylsilane

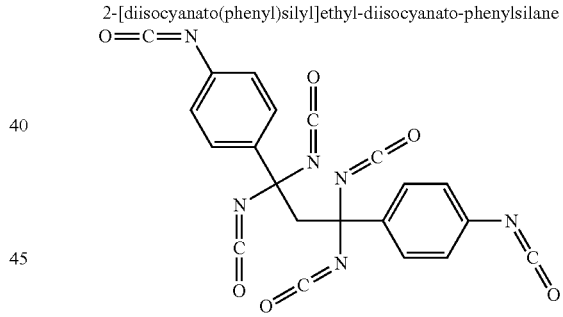

1-isocyanato-4-[1,1,3,3-tetraisocyanato-3-(4-isocyanatophenyl)propyl]benzene

In some embodiments, the cyanate based compound does not include difluoro(isocyanato)phosphane. In some embodiments, the cyanate based compound does not include ethylphophonic diisocyanate.

The concentration of the cyanate based compound in the electrolyte may be about 10% or less, about 0.1% to about 10%, including from about 1% to about 5%, and from about 1% to about 3%; about 10% to about 40%, including from about 10% to about 30%, and from about 20% to about 40% by weight.

A Li-containing salt for a Li-ion battery may include, but not limited to, lithium hexafluorophosphate ($LiPF_6$). In some implementations, a lithium-containing salt for a Li-ion battery may comprise one or more of lithium tetrafluoroborate ($LiBF_4$), lithium hexafluoroarsenate monohydrate ($LiAsF_6$), lithium perchlorate ($LiClO_4$), lithium bis(trifluoromethanesulfonyl)imide (LiTFSI), lithium bis(fluorosulfonyl)imide (LiFSI), lithium bis(oxalato)borate (LiBOB), lithium difluoro(oxalate)borate (LiDFOB), lithium triflate (LiCF$_3$SO$_3$), lithium tetrafluorooxalato phosphate (LTFOP), lithium difluorophosphate (LiPO$_2$F$_2$), lithium pentafluoroethyltrifluoroborate (LiFAB), and lithium 2-trifluoromethyl-4,5-dicyanoimidazole (LiTDI), lithium bis(2-fluoromalonato)borate (LiBFMB), lithium 4-pyridyl trimethyl borate (LPTB) and lithium 2-fluorophenol trimethyl borate (LFPTB), lithium catechol dimethyl borate (LiCDMB), etc. The electrolyte can have a salt concentration of about 1 moles/L (M) or more. The electrolyte can also have a salt concentration of about 1.2 M, about 1.5M, or more.

In some implementations, the electrolyte system can include FEC, EMC, a cyanate based compound as disclosed herein, and a Li-containing salt. The Li-containing salt may be LiPF$_6$. The concentration of FEC may be about 5% or more, about 10% or more, from about 20% to about 40%, including about 20%, about 30%, and about 40% by weight. The concentration of EMC may be from about 30% to about 60%, including about 30%, about 40%, about 50%, and about 60% by weight. The concentration of a cyanate based compound may be about 10% or less, from about 10% to about 50%, including from about 10% to about 40 vol %, about 10%, about 20%, about 30%, and about 40% by weight.

The electrolyte may include additional additives, such as an oxygen-containing electrolyte additive, a sulfur-containing compounds, a fluorine-containing additive, a silicon-containing additive, a nitrogen-containing additive, a boron-containing additive, a phosphorus-containing additive, etc. In addition to the heterogeneous atoms, these additives may also contain other functional groups, such as C=C bond, C≡C bond, ring structures, etc.

In some implementations, the electrolyte system may contain FEC, EMC, a cyanate based compound as disclosed herein, and a Li-containing salt, without other co-solvent. In some implementations, the electrolyte system may contain FEC, EMC, a cyanate based compound as disclosed herein, and a Li-containing salt, without other additive. In some implementations, the electrolyte is substantially free of non-fluorine containing cyclic carbonate The electrolyte additives, along with the electrolytes, can be reduced or self-polymerize on the surface of Si-based anode to form a SEI layer that can reduce or prevent the crack and/or the continuous reduction of electrolyte solutions as the Si containing anode expands and contracts during cycling. Furthermore, these electrolyte additives, along with the electrolyte solvents, may be oxidized on a cathode surface to form a CEI layer that can suppress or minimize further decomposition of the electrolyte on the surface of the cathode. Without being bound to the theory or mode of operation, it is believed that the presence of cyanate based compounds in the electrolyte can result in a SEI and/or CEI layer on the surface of electrodes with improved performance. An SEI layer comprising a cyanate based compound may demonstrate improved chemical stability and increased density, for example, compared to SEI layers formed by electrolytes without additives or with traditional additives. As such, the change in thickness and surface reactivity of the interface layer are limited, which may in turn facilitate reduction in capacity fade and/or generation of excessive gaseous byproducts during operation of the Li-ion battery. A CEI layer comprising a cyanate based compound may help minimize the transition metal ion dissolutions and structure changes on cathode side and may provide favorable kinetics resulting in improved cycling stability and rate capability. In some embodiments, electrolyte solvents comprising cyanate based compounds may be less flammable and more flame retardant.

Electrodes

The cathode for the energy storage device may include Li transition metal oxide cathode materials, such as Lithium cobalt oxide (LiCoO$_2$) (LCO), lithium (Li)-rich oxides/layer oxides, nickel (Ni)-rich oxide/layered oxides, high-voltage spinel oxides, and high-voltage polyanionic compounds. Ni-rich oxides/layered oxides may include lithium nickel cobalt manganese oxide (LiNi$_x$Co$_y$Mn$_z$O$_2$, x+y+z=1, "NCM"), lithium nickel cobalt aluminum oxide (LiNi$_a$Co$_b$Al$_c$O$_2$, a+b+c=1, "NCA"), LiNi$_{1-x}$M$_x$O$_2$ and LiNi$_{1+x}$M$_{1-x}$O$_2$ (where M=Co, Mn or Al). Examples of a NCM material include LiNi$_{0.6}$Co$_{0.2}$Mn$_{0.2}$O$_2$ (NCM-622), NCM-111, NC-433, NCM-523, NCM-811, and NCM-9 0.5 0.5. Li-rich oxides/layered oxides may include Li$_y$Ni$_{1+x}$M$_{1-x}$O$_2$ (where y>1, and M=Co, Mn or Al), xLi$_2$MnO$_3$·(1-x)LiNi$_a$Co$_b$Mn$_c$O$_2$, and xLi$_2$Mn$_3$O$_2$·(1-x)LiNi$_a$Co$_b$Mn$_c$O$_2$. High-voltage spinel oxides may include lithium manganese spinel (LiMn$_2$O$_4$, "LMO") or lithium nickel manganese spinel (LiNi$_{0.5}$Mn$_{1.5}$O$_4$, "LNMO"). High-voltage polyanionic compounds may include phosphates, sulfates, silicates, titanate, etc. One example of polyanionic compound may be lithium iron phosphate (LiFePO$_4$, "LFP").

In order to increase volumetric and gravimetric energy density of Li-ion batteries, silicon may be used as the active material for the anode. Thus, the anode for the energy storage device include Si-based anode. Several types of silicon materials, e.g., silicon nanopowders, silicon nanofibers, porous silicon, and ball-milled silicon, are viable candidates as active materials for the anode. Alternatively, as described in U.S. patent application Ser. Nos. 13/008,800 and 13/601,976, entitled "Composite Materials for Electrochemical Storage" and "Silicon Particles for Battery Electrodes," a Si-based anode can also contain a composite material film that includes Si particles distributed in a carbon phase. The Si-based anode can include one or more types of carbon phases. At least one of these carbon phases is a substantially continuous phase that extends across the entire film and holds the composite material film together. The Si particles are distributed throughout the composite material film.

The composite material film may be formed by pyrolyzing a mixture comprising a precursor (such as a polymer or a polymer precursor) and Si particles. The mixture can optionally further contain graphite particles. Pyrolyzation of the precursor forms a pyrolytic carbon and results in one or more type of carbon phases. In some implementations, the composite material film can have a self-supporting monolithic structure, and therefore is a self-supporting composite material film. Because the precursor is converted into an electrically conductive and electrochemically active matrix, the resulting electrode is conductive enough that, in some cases, a metal foil or mesh current collector can be omitted or minimized. The converted polymer also acts as an expansion buffer for Si particles during cycling so that a high cycle life can be achieved. In certain implementations, the resulting electrode is an electrode that is comprised substantially of active material. The electrodes can have a high energy density of between about 500 mAh/g to about 1200 mAh/g. The composite material film may also be used as a cathode active material in some electrochemical couples with additional additives.

The amount of carbon obtained from the precursor can be from about 2% to about 50%, from about 2% to about 40%, from about 2% to about 30%, from about 2% to about 25%, or from about 2% to about 20% by weight of the composite material. The carbon is obtained through heating a carbon-containing precursor at a temperature sufficient for pyrolysis of the precursor to occur, and is thus a pyrolytic carbon. The carbon from the precursor can be hard and/or soft carbon. Hard carbon can be a carbon that does not convert into graphite even with heating in excess of 2800 degrees Celsius. Precursors that melt or flow during pyrolysis convert into soft carbons and/or graphite with sufficient temperature and/or pressure. The hard carbon phase can be a matrix phase in the composite material. The hard carbon can also be embedded in the pores of the additives including silicon. The hard carbon may react with some of the additives to create some materials at interfaces. For example, there may be a silicon carbide layer or silicon carbide containing oxygen (Si—C—O) layer between silicon particles and the pyrolytic carbon. Possible pyrolytic carbon precursors can include polyimide (or a polyimide precursor), other aromatic polyimides, phenolic resins, epoxy resins, poly(p-phenylene vinylene) (PPV), poly(p-phenylene-1,3,4-oxadiazole) (POD), benzimidazobenzophenanthroline ladder (BBL) polymer, and other polymers that have a very high melting point or are cross-linked.

The amount of Si particles in the composite material may be between greater than 0% and about 90% by weight, between about 20% and about 80%, between about 30% and about 80%, or between about 40% and about 80%. In some implementations, the amount of Si particles in the composite material may be between about 50% and about 90% by weight, between about 50% and about 80%, or between about 50% and about 70%, and such anode is considered as a Si-dominant anode. The amount of one or more types of carbon phases in the composite material may be between greater than 0% and about 90% by weight or between about 1% and about 70% by weight. The pyrolyzed/carbonized polymer can form a substantially continuous conductive carbon phase in the entire electrode as opposed to particulate carbon suspended in a non-conductive binder in one class of conventional lithium-ion battery electrodes.

The largest dimension of the silicon particles can be less than about 40 μm, less than about 1 μm, between about 10 nm and about 40 μm, between about 10 nm and about 1 μm, less than about 500 nm, less than about 100 nm, and about 100 nm. All, substantially all, or at least some of the silicon particles may comprise the largest dimension described above. For example, an average or median largest dimension of the silicon particles can be less than about 40 μm, less than about 1 μm, between about 10 nm and about 40 μm, between about 10 nm and about 1 μm, less than about 500 nm, less than about 100 nm, and about 100 nm. Furthermore, the silicon particles may or may not be pure silicon. For example, the silicon particles may be substantially silicon or may be a silicon alloy. The silicon alloy includes silicon as the primary constituent along with one or more other elements.

Micron-sized silicon particles can provide good volumetric and gravimetric energy density combined with good cycle life. In certain implementations, to obtain the benefits of both micron-sized silicon particles (e.g., high energy density) and nanometer-sized silicon particles (e.g., good cycle behavior), silicon particles can have an average particle size in the micron range and a surface including nanometer-sized features. The silicon particles have an average particle size (e.g., average diameter or average largest dimension) between about 0.1 am and about 30 μm or between about 0.1 am and all values up to about 30 μm. For example, the silicon particles can have an average particle size between about 0.5 am and about 25 μm, between about 0.5 am and about 20 am, between about 0.5 μm and about 15 μm, between about 0.5 μm and about 10 μm, between about 0.5 μm and about 5 μm, between about 0.5 μm and about 2 μm, between about 1 μm and about 20 μm, between about 1 μm and about 15 μm, between about 1 μm and about 10 μm, between about 5 μm and about 20 μm, etc. Thus, the average particle size can be any value between about 0.1 μm and about 30 μm, e.g., about 0.1 μm, about 0.5 μm, about 1 μm, about 5 μm, about 10 μm, about 15 μm, about 20 μm, about 25 μm, and about 30 μm.

Optionally, conductive particles that may also be electrochemically active are added to the mixture. Such particles can enable both a more electronically conductive composite as well as a more mechanically deformable composite capable of absorbing the large volumetric change incurred during lithiation and de-lithiation. A largest dimension of the conductive particles is between about 10 nanometers and about 100 microns. All, substantially all, or at least some of the conductive particles may comprise the largest dimension described herein. In some implementations, an average or median largest dimension of the conductive particles is between about 10 nm and about 100 microns. The mixture may include greater than 0% and up to about 80% by weight conductive particles. The composite material may include about 45% to about 80% by weight conductive particles. The conductive particles can be conductive carbon including carbon blacks, carbon fibers, carbon nanofibers, carbon nanotubes, graphite, graphene, etc. Many carbons that are considered as conductive additives that are not electrochemically active become active once pyrolyzed in a polymer matrix. Alternatively, the conductive particles can be metals or alloys, such as copper, nickel, or stainless steel.

For example, graphite particles can be added to the mixture. Graphite can be an electrochemically active material in the battery as well as an elastic deformable material that can respond to volume change of the silicon particles. Graphite is the preferred active anode material for certain classes of lithium-ion batteries currently on the market because it has a low irreversible capacity. Additionally, graphite is softer than pyrolytic carbon, in certain directions of force, and can better absorb the volume expansion of silicon additives. Preferably, a largest dimension of the graphite particles is between about 0.5 microns and about 100 microns. All, substantially all, or at least some of the graphite particles may comprise the largest dimension described herein. In some implementations, an average or median largest dimension of the graphite particles is between about 0.5 microns and about 100 microns. The mixture may include about 2% to about 50% by weight of graphite particles. The composite material may include about 40% to about 75% by weight graphite particles.

The composite material may also be formed into a powder. For example, the composite material can be ground into a powder. The composite material powder can be used as an active material for an electrode. For example, the composite material powder can be deposited on a collector in a manner similar to making a conventional electrode structure, as known in the industry.

In some embodiments, the full capacity of the composite material may not be utilized during use of the battery to improve battery life (e.g., number charge and discharge cycles before the battery fails or the performance of the battery decreases below a usability level). For example, a composite material with about 70% by weight silicon particles, about 20% by weight carbon from a precursor, and about 10% by weight graphite may have a maximum gravimetric capacity of about 2000 mAh/g, while the composite material may only be used up to a gravimetric capacity of about 550 to about 850 mAh/g. Although, the maximum gravimetric capacity of the composite material may not be utilized, using the composite material at a lower capacity can still achieve a higher capacity than certain lithium ion batteries. In certain embodiments, the composite material is used or only used at a gravimetric capacity below about 70% of the composite material's maximum gravimetric capacity. For example, the composite material is not used at a gravimetric capacity above about 70% of the composite material's maximum gravimetric capacity. In further embodiments, the composite material is used or only used at a gravimetric capacity below about 50% of the composite material's maximum gravimetric capacity or below about 30% of the composite material's maximum gravimetric capacity.

Pouch Cell

As described herein, a battery can be implement as a pouch cell. FIG. 1 shows a cross-sectional schematic diagram of an example of a Li-ion battery 300 implemented as a pouch cell. The battery 300 comprises an anode 316 in contact with a negative current collector 308, a cathode 304 in contact with a positive current collector 310, a separator 306 disposed between the anode 316 and the cathode 304. A plurality of anodes 316 and cathode 304 may also be arranged into a stacked configuration with the separator 306 separating each anode 316 and cathode 304. Each negative current collector 308 may have one anode 316 attached to each side; each positive current collector 310 may have one cathode 304 attached to each side. The stacks are immersed in an electrolyte 314 and enclosed in a pouch 312. The anode 302 and the cathode 304 may comprise one or more respective electrode films formed thereon. The number of electrodes in the battery 300 may be selected to provide desired device performance.

With further reference to FIG. 1, the separator 306 may comprise a single continuous or substantially continuous sheet, which can be interleaved between adjacent electrodes of the electrode stack. For example, the separator 306 may be shaped and/or dimensioned such that it can be positioned between adjacent electrodes in the electrode stack to provide desired separation between the adjacent electrodes of the battery 300. The separator 306 may be configured to facilitate electrical insulation between the anode 302 and the cathode 304, while permitting ionic transport between the anode 302 and the cathode 304. The separator 306 may comprise a porous material, such as a porous polyolefin material. However, the separator material is not particularly limited.

The Li-ion battery 300 may include an electrolyte 314, for example an electrolyte having a composition as described herein. The electrolyte 314 is in contact with the anode 302, the cathode 304, and the separator 306.

With continued reference to FIG. 1, the anode 302, cathode 304 and separator 306 of the Li-ion battery 300 may be enclosed in a housing comprising a pouch 312. In some embodiments, the pouch 312 may comprise a flexible material, so it may readily deform upon application of pressure on the pouch 312, including pressure exerted upon the pouch 312 from within the housing. For example, the pouch 312 may comprise a laminated aluminum pouch.

In some embodiments, the Li-ion battery 300 may comprise an anode connector (not shown) and a cathode connector (not shown) configured to electrically couple the anodes and the cathodes of the electrode stack to an external circuit, respectively. The anode connector and a cathode connector may be affixed to the pouch 312 to facilitate electrical coupling of the battery 300 to an external circuit. The anode connector and the cathode connector may be affixed to the pouch 312 along one edge of the pouch 312. The anode connector and the cathode connector can be electrically insulated from one another, and from the pouch 312. For example, at least a portion of each of the anode connector and the cathode connector can be within an electrically insulating sleeve such that the connectors can be electrically insulated from one another and from the pouch 312.

A Li-ion battery comprising an electrolyte composition as described herein, and an anode having a composite active material film as described herein, may demonstrate reduced gassing and/or swelling at room temperature (e.g., about 20° C. to about 25° C.) or elevated temperatures (e.g., up to about 85° C.), increased cycle life at room temperature or elevated temperatures, and/or reduced cell growth/electrolyte consumption per cycle, for example compared to Li-ion batteries comprising conventionally available electrolyte compositions in combination with an anode having the same active material. In some embodiments, the Li-ion battery as described herein may demonstrate reduced gassing and/or swelling across various temperatures at which the battery may be subject to testing, such as temperatures between about −20° C. and about 130° C. (e.g., compared to the same Li-ion batteries comprising conventionally available electrolyte compositions).

Gaseous byproducts may be undesirably generated during battery operation, for example, due to chemical reactions between the electrolyte and one or more other components of the Li-ion battery, such as one or more components of a battery electrode. Excessive gas generation during operation of the Li-ion battery may adversely affect battery performance and/or result in mechanical and/or electrical failure of the battery. For example, undesired chemical reactions between an electrolyte and one or more components of an anode may result in gas generation at levels which can mechanically (e.g., structural deformation) and/or electrochemically degrade the battery. Thus, the composition of the anode and the composition of the electrolyte can be selected to reduced gas generation.

EXAMPLES

Exemplified Li-ion batteries and processes for device fabrication are described below, and the performances of Li-ion batteries with different electrolytes and electrolyte additives are evaluated.

Example 1

In Example 1, 0.25 wt % or 0.5 wt % of allyl isocyanate (AlSOCY) were added to 1.2M LiPF$_6$ in FEC/EMC (3/7 wt %)-based electrolytes and their electrochemical performances in Si-dominant anode//NCA cathode coin full cells were evaluated. The corresponding coin cells and 5 layer pouch cells were built with Si-dominant anodes and NCA cathodes. The coin cells were tested at 1C/0.5C charge/discharge cycle regime with the working voltage window of 4.2V to 3.1V at room temperature. The pouch cells were tested at 4C/0.5C charge/discharge cycle regime with the working voltage window of 4.2V to 3.1V at room temperature, and at 1C/0.5C charge/discharge cycle regime with the working voltage window of 4.2V to 3.1V at 45° C.

Figure 2A:
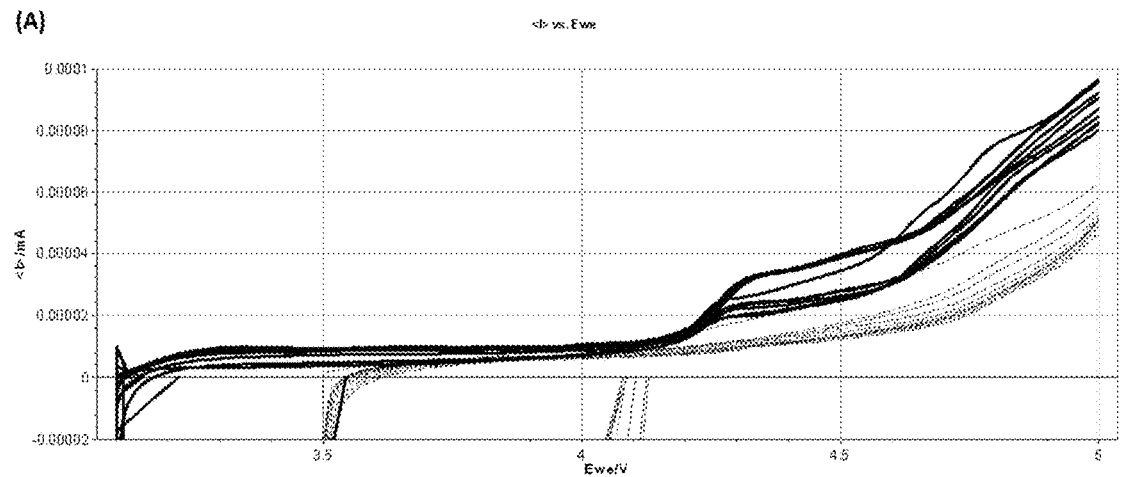
FIGS. 2A and 2B show Linear sweep voltammetry (LSV) charts of electrolytes using a Pt($W_e$)/Li($C_e$)/Li(ref) three-electrode cell with a scan rate of 1 mV/s.
Figure 2B:
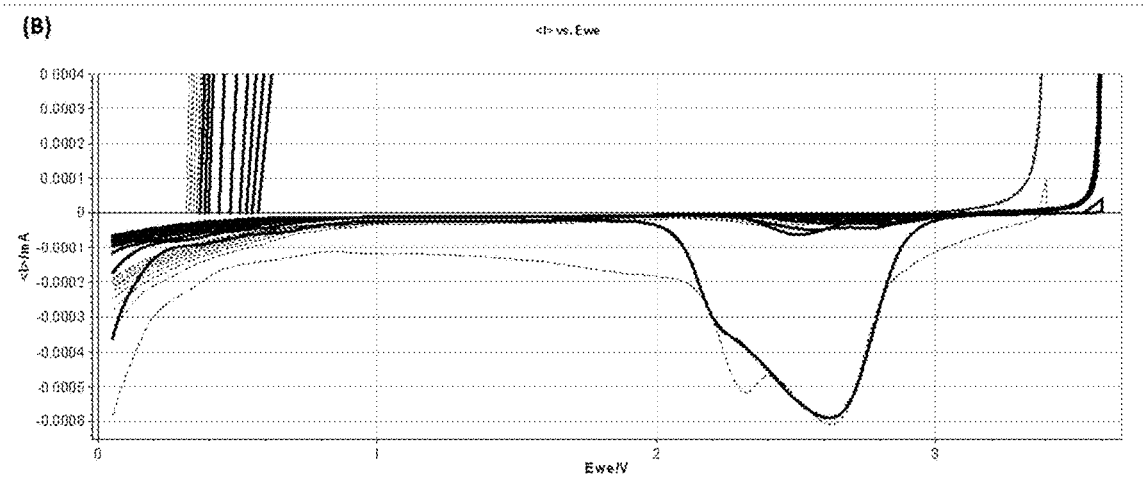

FIGS. 2A and 2B show Linear sweep voltammetry (LSV) of electrolytes using a Pt($W_e$)/Li($C_e$)/Li(ref) three-electrode cell with a scan rate of 1 mV/s. FIG. 2A depicts an Oxidation sweep, and FIG. 2B depicts a reduction sweep. The electrolytes used were: (dotted line) 1.2 M LiPF$_6$ in FEC/EMC (3/7 wt %)–Control, (solid line) 1.2M LiPF$_6$ in FEC/EMC (3/7 wt %)+0.5 wt % AlSOCY.

FIGS. 2A and 2B shows that AlSOCY is readily oxidized on the surface of the cathode from the 1$^{st}$ scanning cycle oxidation sweep. Subsequently, the peak intensity decreases sharply, indicating that 0.5 wt % AlSOCY has passivated the surface, thus forming a stable cathode passivation layer. There is no reduction peak with 0.5 wt % AlSOCY-containing electrolyte seen in the reduction sweep. In addition, the reduction peak from FEC also disappears at the presence of the AlSOCY additive.

Figure 3A:
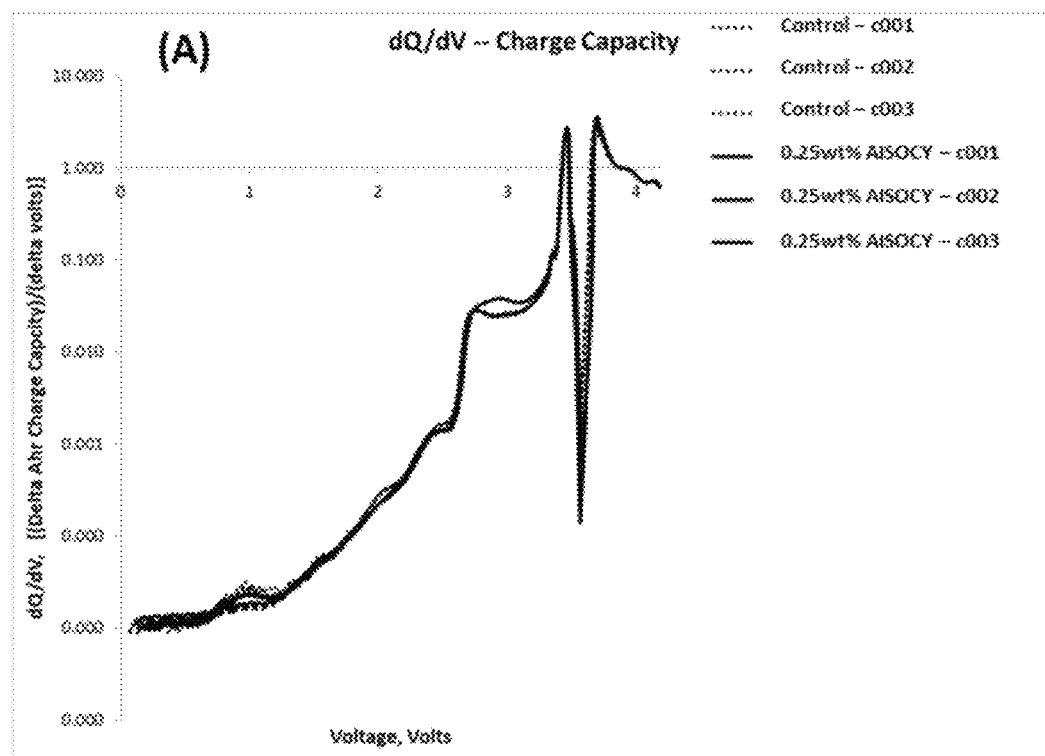
FIGS. 3A and 3B show the charge (A) and discharge (B) curves of an embodiment of Si-dominant anode//NCA cathode full cells, respectively.
Figure 3B:
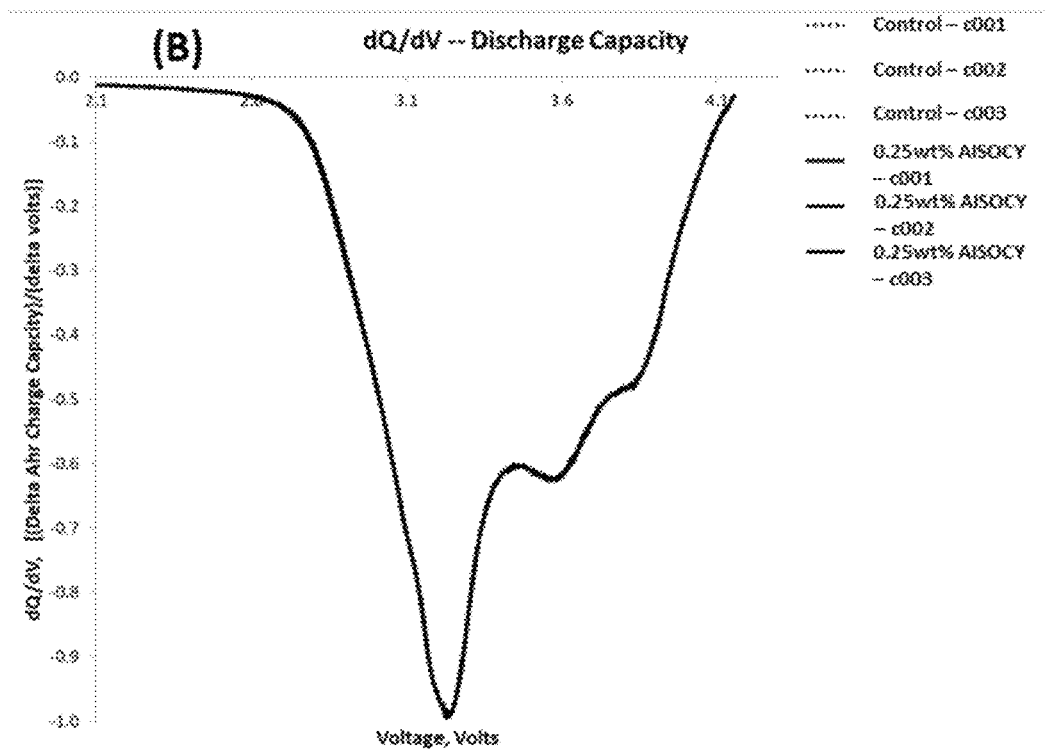

FIGS. 3A and 3B show dQ/dV During Charge (A) and dQ/dV During Discharge (B) curves of Si-dominant anode// NCA cathode full cells. The electrolytes used were: (dotted line) 1.2 M LiPF$_6$ in FEC/EMC (3/7 wt %)–Control, (solid line), 1.2 M LiPF$_6$ in FEC/EMC (3/7 wt %)+0.25 wt % AlSOCY. The Si-dominant anodes contain about 80 wt % Si, 5 wt % graphite and 15 wt % glassy carbon (from resin) and are laminated on 15 μm Cu foil. The average loading is about 3.8 mg/cm$^2$. The cathodes contain about 92 wt % NCA, 4 wt % Super P and 4 wt % PVDF5130, and are coated on 15 μm Al foil. The average loading is about 23 mg/cm$^2$.

The dQ/dV data for both control and 0.25 wt % AlSOCY-containing electrolyte-based cells were obtained through the following testing protocol: Cycle 1: Charge at 0.025C to 25% nominal capacity, charge at 1C to 4.2 V until 0.05C, discharge at 1C to 2 V until 0.2C; Cycle 2: Charge at 1C to 3.3 V until 0.05C, rest 10 minutes.

The 1$^{st}$ formation cycle dQ/dV curves in FIGS. 3A and 3B show that 0.25 wt % AlSOCY-containing electrolyte-based cells have a different curve indicating different reactions occurring on the surface of the electrodes.

Figure 4A:
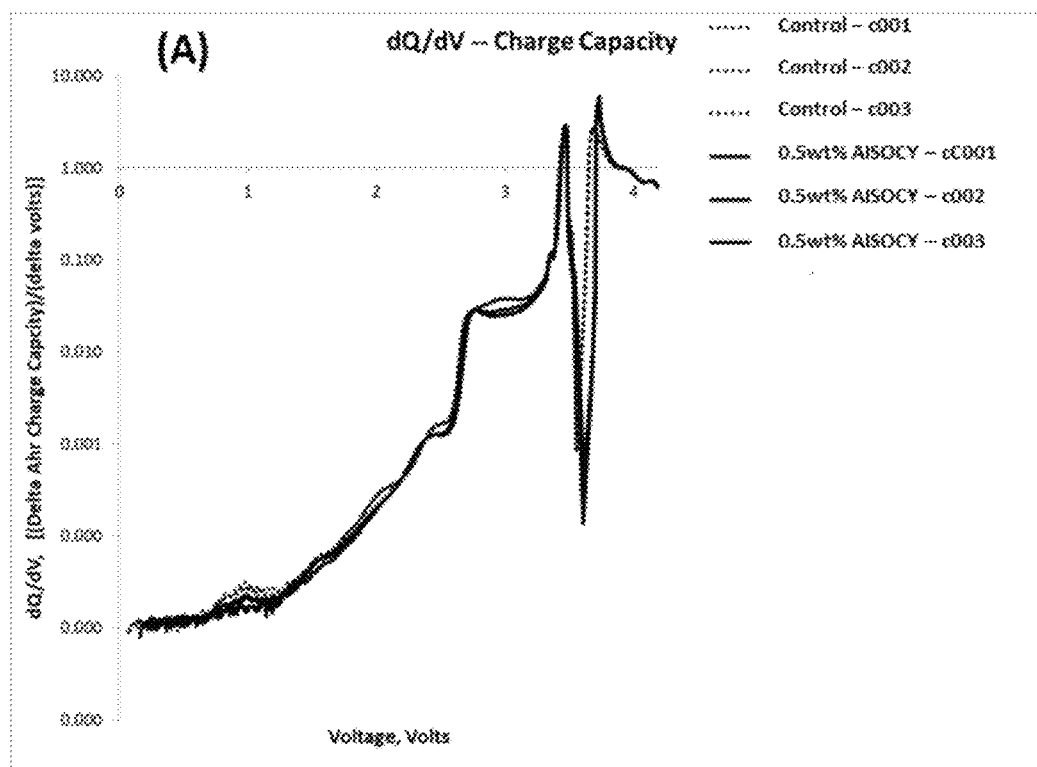
FIGS. 4A and 4B show the charge (A) and discharge (B) curves of an embodiment of Si-dominant anode//NCA cathode full cells, respectively.
Figure 4B:
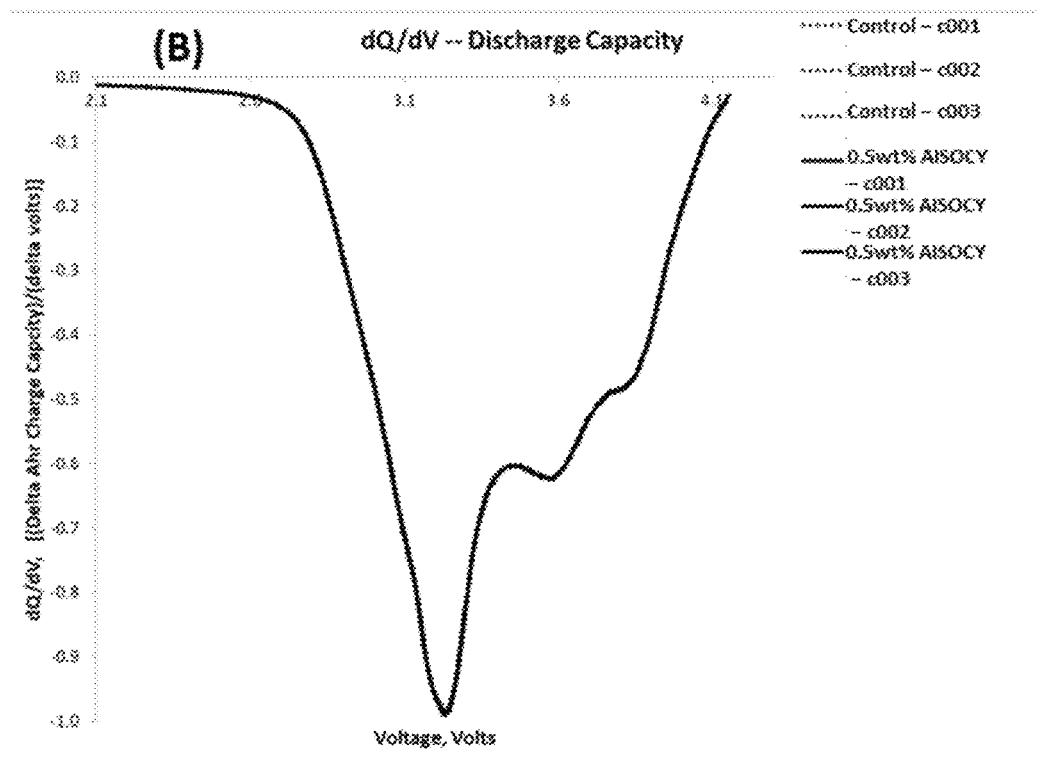

FIGS. 4A and 4B show dQ/dV During Charge (A) and dQ/dV During Discharge (B) curves of Si-dominant anode// NCA cathode full cells. The electrolytes used were: (dotted line) 1.2 M LiPF$_6$ in FEC/EMC (3/7 wt %)–Control, (solid line), 1.2 M LiPF$_6$ in FEC/EMC (3/7 wt %)+0.5 wt % AlSOCY. The Si-dominant anodes contain about 80 wt % Si, 5 wt % graphite and 15 wt % glassy carbon (from resin) and are laminated on 15 μm Cu foil. The average loading is about 3.8 mg/cm$^2$. The cathodes contain about 92 wt % NCA, 4 wt % Super P and 4 wt % PVDF5130, and are coated on 15 μm Al foil. The average loading is about 23 mg/cm$^2$.

The dQ/dV data for both control and 0.5 wt % AlSOCY-containing electrolyte-based cells were obtained through the following testing protocol: Cycle 1: Charge at 0.025C to 25% nominal capacity, charge at 1C to 4.2 V until 0.05C, discharge at 1C to 2 V until 0.2C; Cycle 2: Charge at 1C to 3.3 V until 0.05C, rest 10 minutes.

The 1$^{st}$ formation cycle dQ/dV curves in FIGS. 4A and 4B show that 0.5 wt % AlSOCY-containing electrolyte-based cells have a different curve indicating different reactions occurring on the surface of the Si anodes.

Figure 5A:
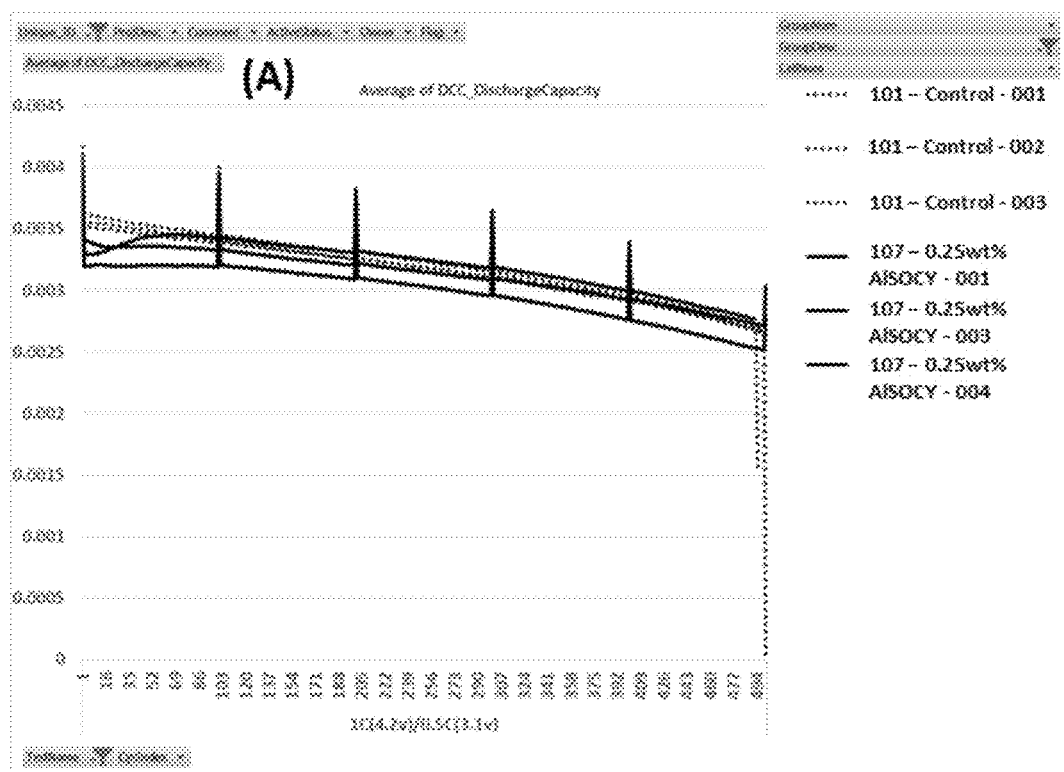
FIGS. 5A and 5B show the capacity retention (A) and normalized capacity retention (B) of an embodiment of Si-dominant anode//NCA cathode full cells, respectively.
Figure 5B:
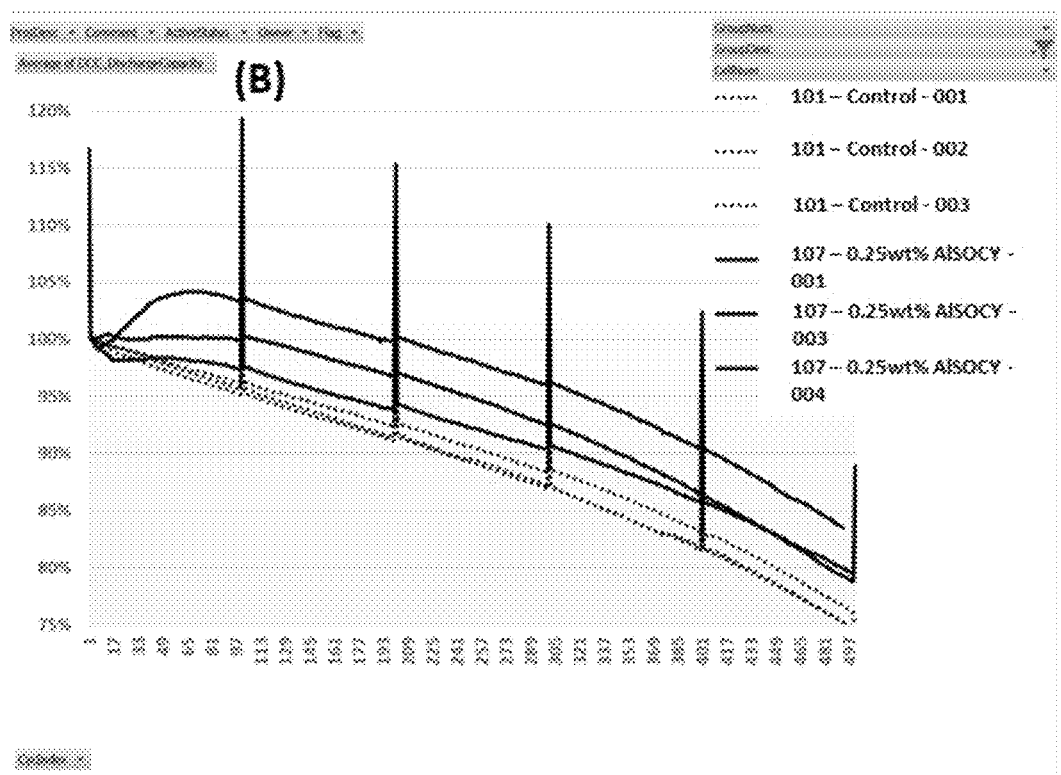

FIGS. 5A and 5B show Capacity retention (A) and (B) Normalized capacity retention of Si-dominant anode//NCA cathode coin full cells. The Si-dominant anodes contain about 80 wt % Si, 5 wt % graphite and 15 wt % glassy carbon (from resin) and are laminated on 15 μm Cu foil. The average loading is about 3.8 mg/cm$^2$. The cathodes contain about 92 wt % NCA, 4 wt % Super P and 4 wt % PVDF5130, and are coated on 15 μm Al foil. The average loading is about 23 mg/cm$^2$. The electrolytes used were: (dotted line) 1.2 M LiPF$_6$ in FEC/EMC (3/7 wt %)–Control, (thick solid line) 1.2 M LiPF$_6$ in FEC/EMC (3/7 wt %)+0.25 wt % AlSOCY. These cells were tested at 25° C.

The long-term cycling program for both control and the 0.25 wt % AlSOCY-containing electrolyte-based cells include: (i) At the 1$^{st}$ cycle, Charge at 0.33C to 4.2 V until 0.05C, rest 5 minutes, discharge at 0.33C to 3.1 V, rest 5 minutes; and (ii) from the 2$^{nd}$ cycle, Charge at 1C to 4.2 V until 0.05C, rest 5 minutes, discharge at 0.5C to 3.1 V, rest 5 minutes. But after every 100 cycles, the test conditions in the 1$^{st}$ cycle were repeated.

FIGS. 5A and 5B indicate the 0.25 wt % AlSOCY-containing electrolyte-based coin full cells have improved cycle performance than the control.

Figure 6A:
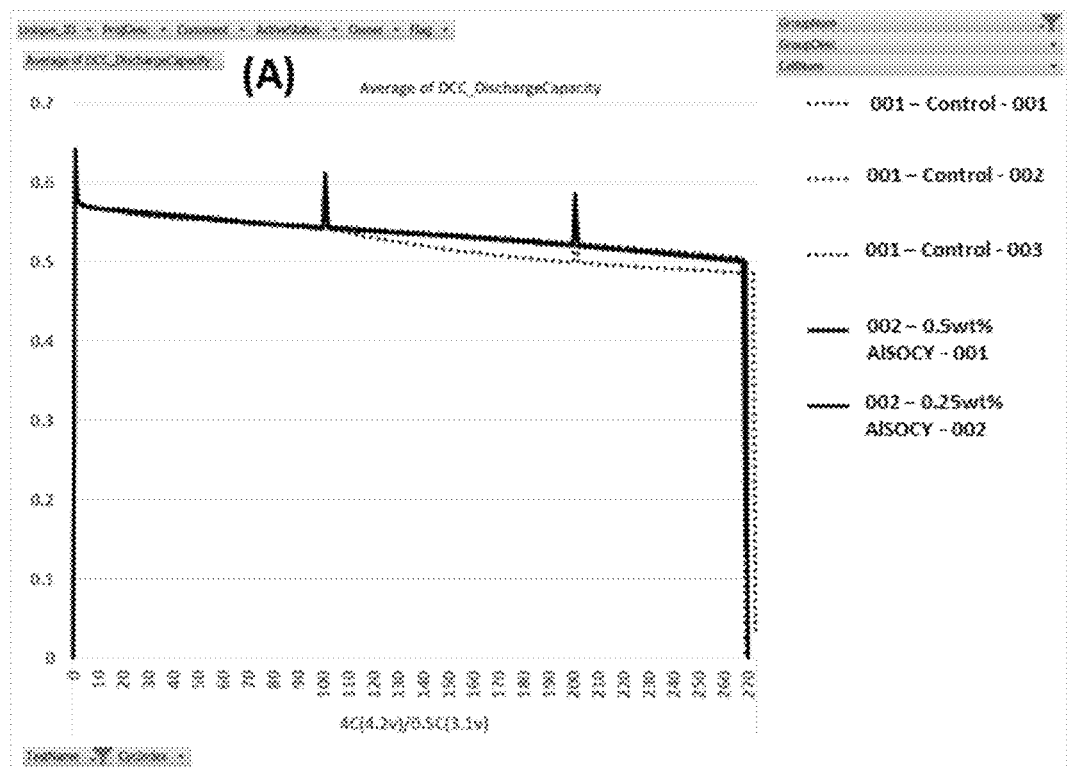
FIGS. 6A and 6B show the capacity retention (A) and normalized capacity retention (B) of an embodiment of Si-dominant anode// NCA cathode full cells, respectively.
Figure 6B:
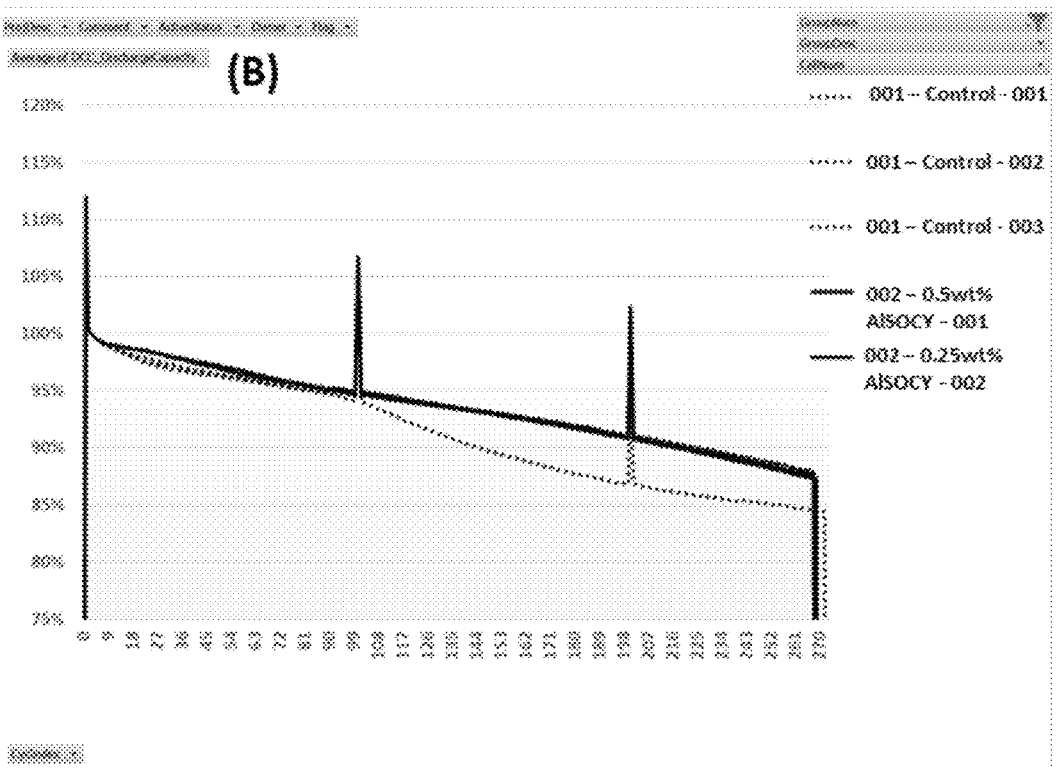

FIGS. 6A and 6B Capacity retention (A) and (B) Normalized capacity retention of Si-dominant anode//NCA cathode pouch full cells. The Si-dominant anodes contain about 80 wt % Si, 5 wt % graphite and 15 wt % glassy carbon (from resin) and are laminated on 15 μm Cu foil. The average loading is about 3.8 mg/cm$^2$. The cathodes contain about 92 wt % NCA, 4 wt % Super P and 4 wt % PVDF5130, and are coated on 15 μm Al foil. The average loading is about 23 mg/cm$^2$. The electrolytes used were: (dotted line) 1.2 M LiPF$_6$ in FEC/EMC (3/7 wt %)–Control, (thick solid line) 1.2 M LiPF$_6$ in FEC/EMC (3/7 wt %)+0.5 wt % AlSOCY. These cells were tested at 25° C.

The long-term cycling program for both control and the 0.5 wt % AlSOCY-containing electrolyte-based cells include: (i) At the 1$^{st}$ cycle, Charge at 0.33C to 4.2 V until 0.05C, rest 5 minutes, discharge at 0.33C to 3.1 V, rest 5 minutes; and (ii) from the 2$^{nd}$ cycle, Charge at 4C to 4.2 V until 0.05C, rest 5 minutes, discharge at 0.5C to 3.1 V, rest 5 minutes. But after every 100 cycles, the test conditions in the 1$^{st}$ cycle were repeated.

FIGS. 6A and 6B indicate the 0.5 wt % AlSOCY-containing electrolyte-based pouch full cells have similar cycle performance with the control in the 5-layer pouch cell studies after about 270 cycles at room temperature.

Figure 7A:
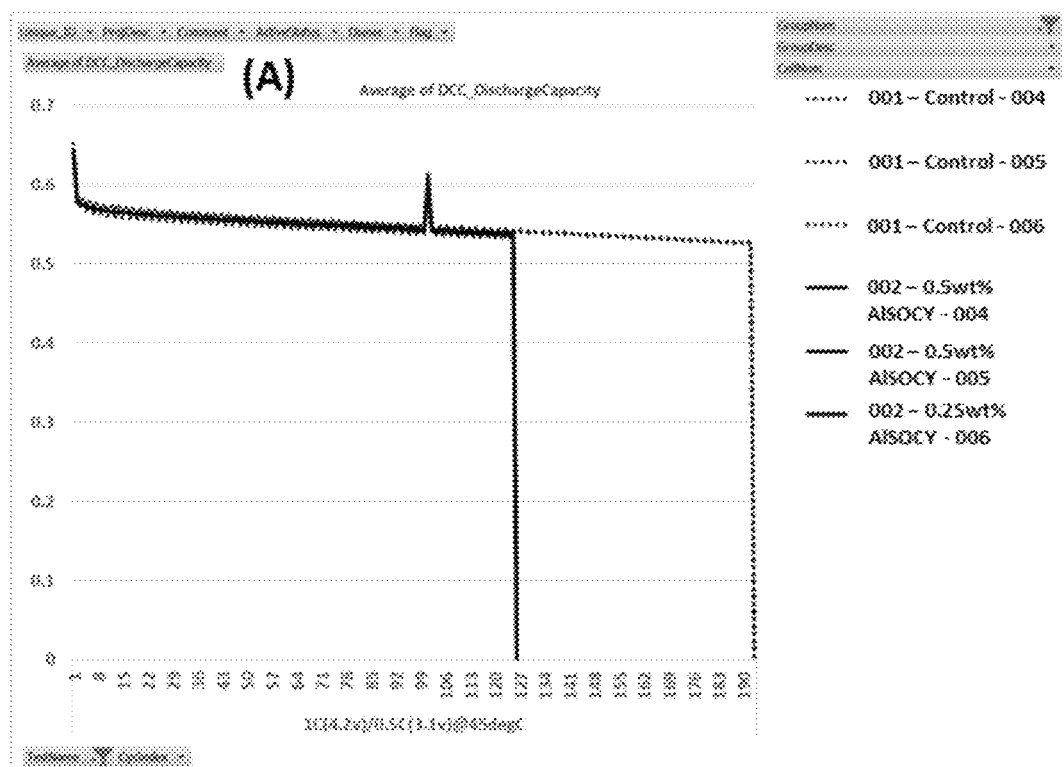
FIGS. 7A and 7B show the capacity retention (A) and normalized capacity retention (B) of an embodiment of Si-dominant anode// NCA cathode full cells, respectively.
Figure 7B:
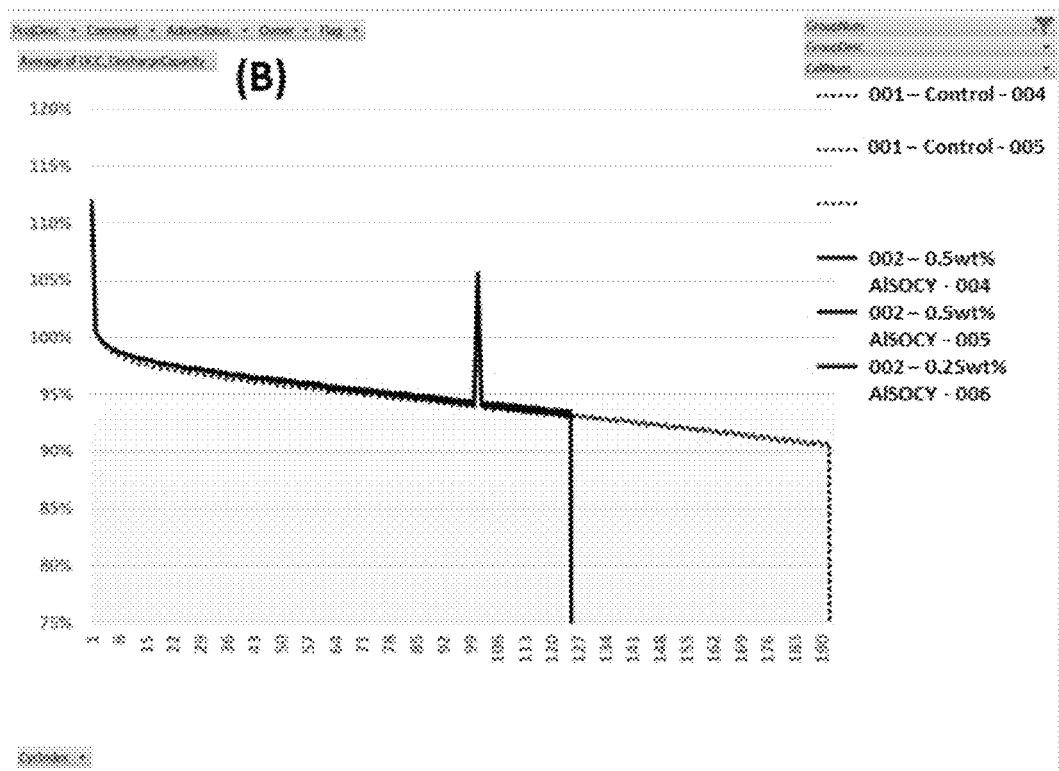

FIGS. 7A and 7B show Capacity retention (A) and (B) Normalized capacity retention of Si-dominant anode//NCA cathode pouch full cells. The Si-dominant anodes contain about 80 wt % Si, 5 wt % graphite and 15 wt % glassy carbon (from resin) and are laminated on 15 μm Cu foil. The average loading is about 3.8 mg/cm$^2$. The cathodes contain about 92 wt % NCA, 4 wt % Super P and 4 wt % PVDF5130, and are coated on 15 μm Al foil. The average loading is about 23 mg/cm$^2$. The electrolytes used were: (dotted line) 1.2 M LiPF$_6$ in FEC/EMC (3/7 wt %)–Control, (thick solid line) 1.2 M LiPF$_6$ in FEC/EMC (3/7 wt %)+0.5 wt % AlSOCY. These cells were tested at 45° C.

The long-term cycling program for both control and the 0.5 wt % AlSOCY-containing electrolyte-based pouch cells include: (i) At the 1$^{st}$ cycle, Charge at 0.33C to 4.2 V until 0.05C, rest 5 minutes, discharge at 0.33C to 3.1 V, rest 5 minutes; and (ii) from the 2$^{nd}$ cycle, Charge at 1C to 4.2 V until 0.05C, rest 5 minutes, discharge at 0.5C to 3.1 V, rest 5 minutes. But after every 100 cycles, the test conditions in the 1$^{st}$ cycle were repeated.

FIGS. 7A and 7B indicate the 0.5 wt % AlSOCY-containing electrolyte-based pouch full cells have similar cycle performance with the control in the 5-layer pouch cell studies after about 130 cycles at 45° C.

Various embodiments have been described above. Although the invention has been described with reference to these specific embodiments, the descriptions are intended to be illustrative and are not intended to be limiting. Various modifications and applications may occur to those skilled in the art without departing from the true spirit and scope of the invention as defined in the appended claims.

What is claimed is:

1. An energy storage device comprising:
   a first electrode;
   a second electrode;
   a separator between the first electrode and the second electrode; and
   an electrolyte system comprising:
      a cyanate based compound;
      a linear carbonate;
      a cyclic carbonate; and
      a Li-containing salt; wherein said cyanate based compound is any one of formulae (VI), (VII) and (VIII):

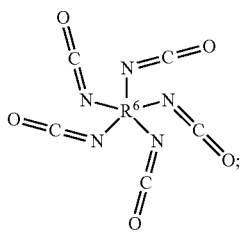

(VI)

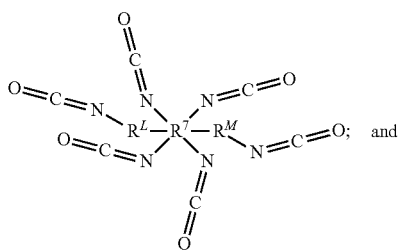

(VII)

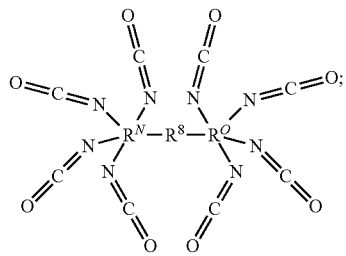

(VIII)

wherein $R^6$, $R^7$ and $R^8$ are each independently selected from the group consisting of a $C_1$-$C_8$ alkylene, $C_2$-$C_8$ alkenylene, a $C_2$-$C_8$ alkynylene, a cycloalkylene, an arylene, —O—,

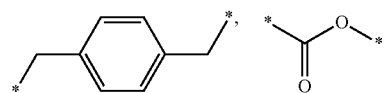

and

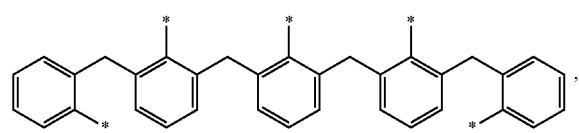

wherein $R^6$, $R^7$ and $R^8$ may be optionally substituted by —F, alkyl, alkenyl, cycloalkyl, aryl, —CN, —N⁺C⁻, fluoro-alkyl, fluoro-ether, —N(CH₃)₂,

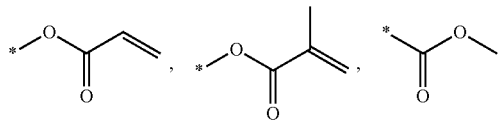

and

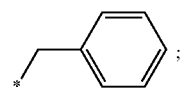

;

wherein $R^L$, $R^M$, $R^N$ and $R^O$ are each independently selected from the group consisting of a bond, a $C_1$-$C_8$ alkylene, a cycloalkylene, an arylene and —Si—, wherein $R^L$, $R^M$, $R^N$ and $R^O$ may be optionally substituted by —F, alkyl, alkenyl, alkynyl and aryl.

2. The energy storage device of claim 1, wherein the linear carbonate is selected from the group consisting of ethyl methyl carbonate (EMC), dimethyl carbonate (DMC), and diethyl carbonate (DEC).

3. The energy storage device of claim 1, wherein the electrolyte system further comprises a co-solvent selected from the group consisting of methyl acetate (MA), ethyl acetate (EA), methyl propanoate, and gamma butyrolactone (GBL).

4. The energy storage device of claim 1, wherein the cyclic carbonate is selected from the group consisting of fluoroethylene carbonate (FEC), di-fluoroethylene carbonate (DiFEC), Trifluoropropylene carbonate (TFPC), ethylene carbonate (EC), vinyl carbonate (VC), propylene carbonate (PC), -fluoromethyl-5-methyl-1,3-dioxolan-2-one (F-t-BC), 3,3-difluoropropylene carbonate (DFPC), and 3,3,4,4,5,5,6,6,6-Nonafluorohexyl-1-ene carbonate.

5. The energy storage device of claim 1, wherein the cyclic carbonate is a fluorine containing cyclic carbonate.

6. The energy storage device of claim 5, wherein the fluorine containing cyclic carbonate is FEC at a concentration of about 5% or more.

7. The energy storage device of claim 1, wherein the electrolyte is substantially free of non-fluorine containing cyclic carbonate.

8. The energy storage device of claim 1, wherein the Li-containing salt is a fluorinated Li salt.

9. The energy storage device of claim 1, wherein the Li-containing salt has a concentration of about 1 M or more.

10. The energy storage device of claim 1, wherein at least one of the first electrode and the second electrode is a Si-base electrode.

11. The energy storage device of claim 10, wherein the Si-based electrode is an anode.

12. The energy storage device of claim 11, wherein the anode is a Si-dominant anode.

13. The energy storage device of claim 11, wherein the anode comprises:
   greater than 0% and less than about 99% by weight of Si particles, and
   greater than 0% and less than about 90% by weight of one or more types of carbon phases, wherein at least one of the one or more types of carbon phases is a substantially continuous phase that holds the composite material film together such that the silicon particles are distributed throughout the composite material film.

14. The energy storage device of claim 13, wherein the anode comprises greater than 50% and less than about 97% by weight of Si particles.

\* \* \* \* \*